United States Patent [19]

Graf

[11] Patent Number: 5,270,337

[45] Date of Patent: Dec. 14, 1993

[54] OXYGEN REMOVAL

[75] Inventor: Ernst Graf, Coon Rapids, Minn.

[73] Assignee: The Pillsbury Company, Minneapolis, Minn.

[21] Appl. No.: 672,132

[22] Filed: Mar. 19, 1991

Related U.S. Application Data

[63] Continuation of Ser. No. 279,604, Dec. 5, 1988, abandoned, which is a continuation of Ser. No. 100,971, Sep. 25, 1987, abandoned.

[51] Int. Cl.$^5$ .................. A23L 3/00; A61K 31/30; A61K 31/34
[52] U.S. Cl. .................................. 514/499; 514/474; 426/132; 426/133
[58] Field of Search .............. 514/499, 474; 426/132, 426/133

[56] References Cited

U.S. PATENT DOCUMENTS

| | | | |
|---|---|---|---|
| 2,772,243 | 11/1956 | Bentz . | |
| 2,892,718 | 7/1959 | Stone | 99/48 |
| 3,294,825 | 12/1966 | Pottier | 260/398.5 |
| 3,320,046 | 5/1967 | Siegel | 71/2.4 |
| 4,384,972 | 5/1983 | Nakamura et al. | 252/188.21 |
| 4,510,162 | 4/1985 | Nezat | 252/188.28 X |
| 4,524,015 | 6/1985 | Takahashi et al. | 252/188.28 |
| 4,559,234 | 12/1985 | Rubin et al. | 426/250 |
| 4,588,561 | 5/1986 | Aswell et al. | 252/182.28 X |
| 4,652,435 | 3/1987 | Natsuume et al. | 252/400.53 X |
| 4,797,274 | 1/1989 | Niki et al. | 424/76.1 |
| 4,818,548 | 4/1989 | Cheng | 426/256 |

FOREIGN PATENT DOCUMENTS 118344 11/1980 Japan .

Primary Examiner—Frederick E. Waddell
Assistant Examiner—K. Weddington
Attorney, Agent, or Firm—Browdy and Neimark

[57] ABSTRACT

An oxygen scavenging composition for use with foods, cosmetics, and pharmaceuticals comprising a combination of a metal that can exist in two redox states at ambient conditions, and a radical oxygen scavenger. The oxygen scavenging system is also effective in inhibiting the growth of yeasts, molds, and most aerobic bacteria.

18 Claims, 31 Drawing Sheets

GAS GENERATION FROM OXYSORB SYSTEM
EFFECT OF ASCORBATE CONCENTRATION AT pH 3

EFFECT OF pH ON O₂ UTILIZATION

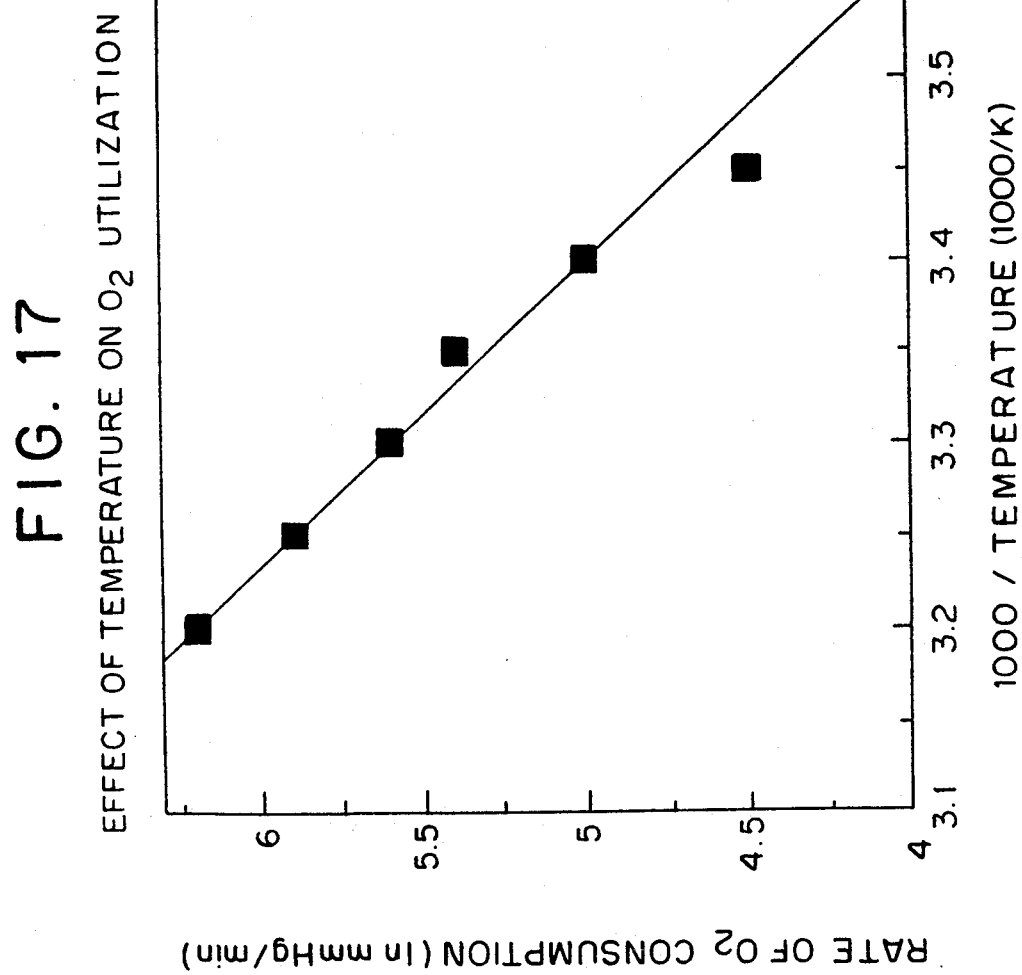

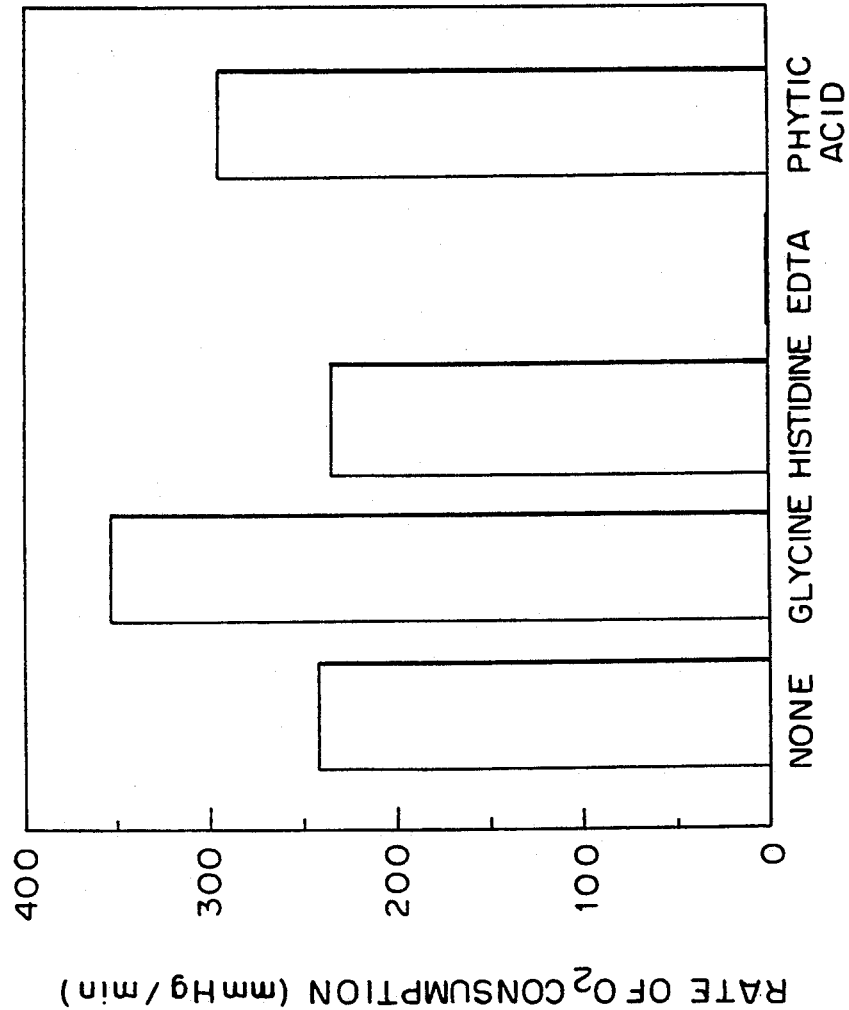

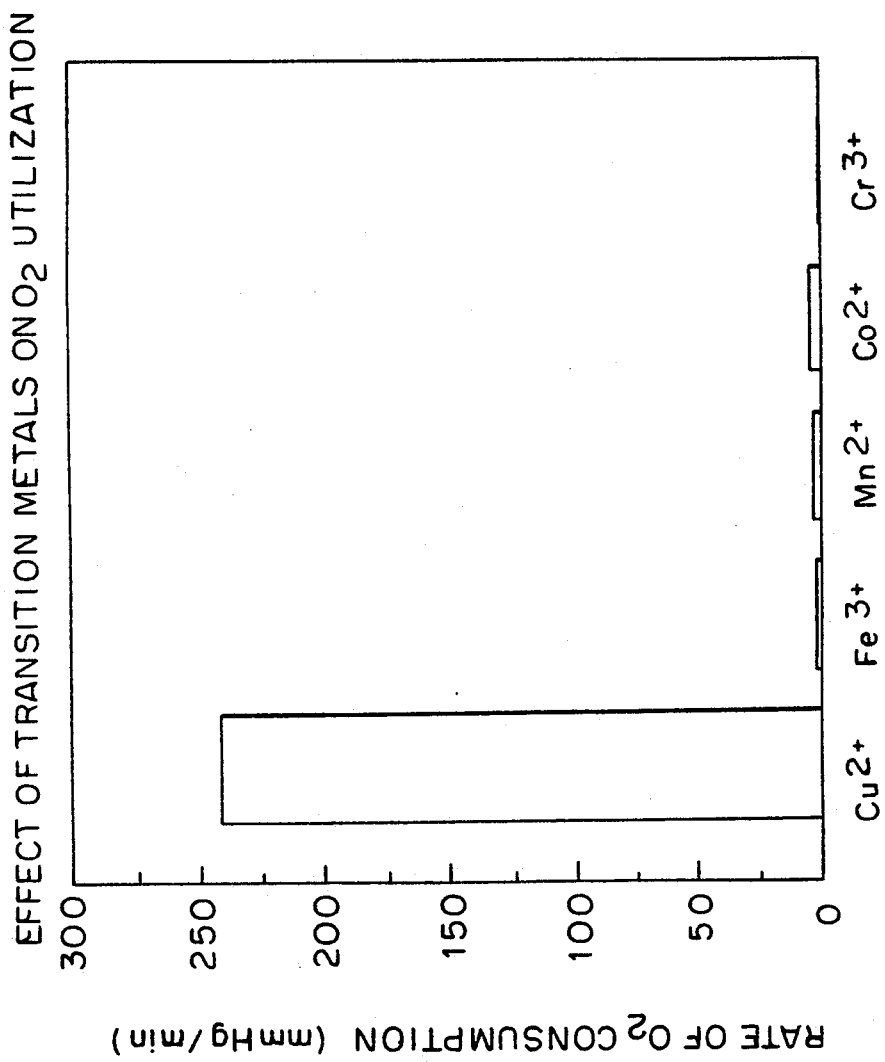

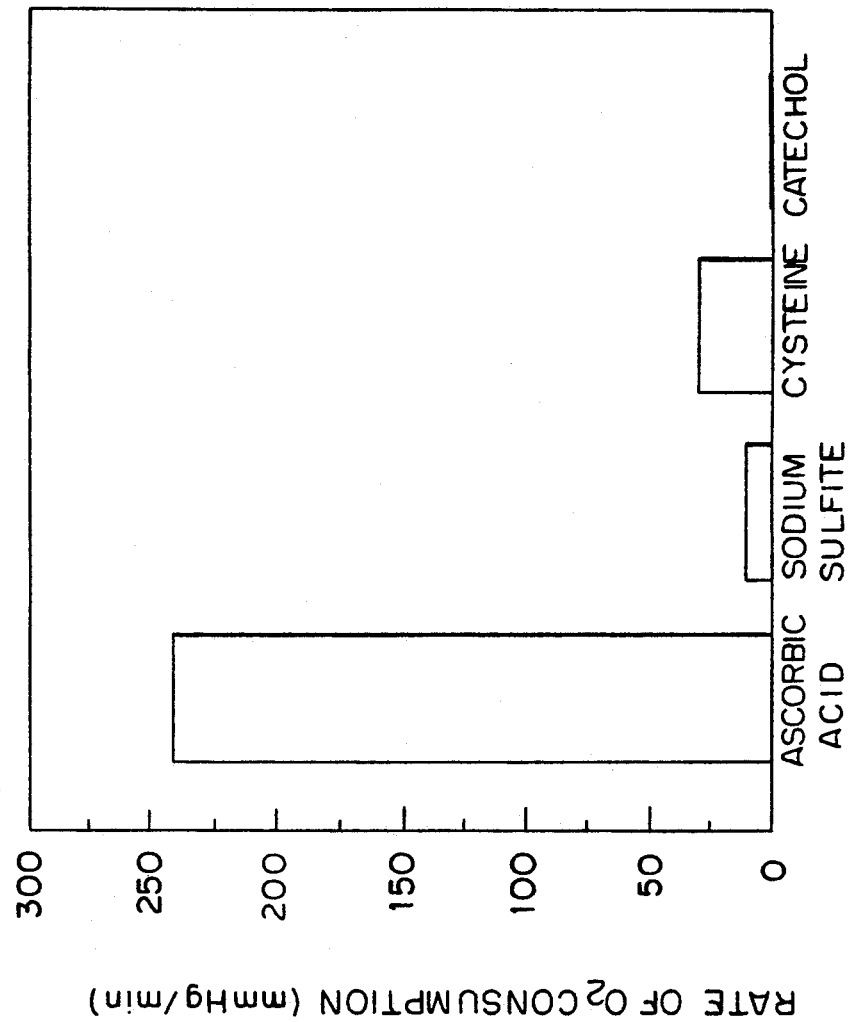

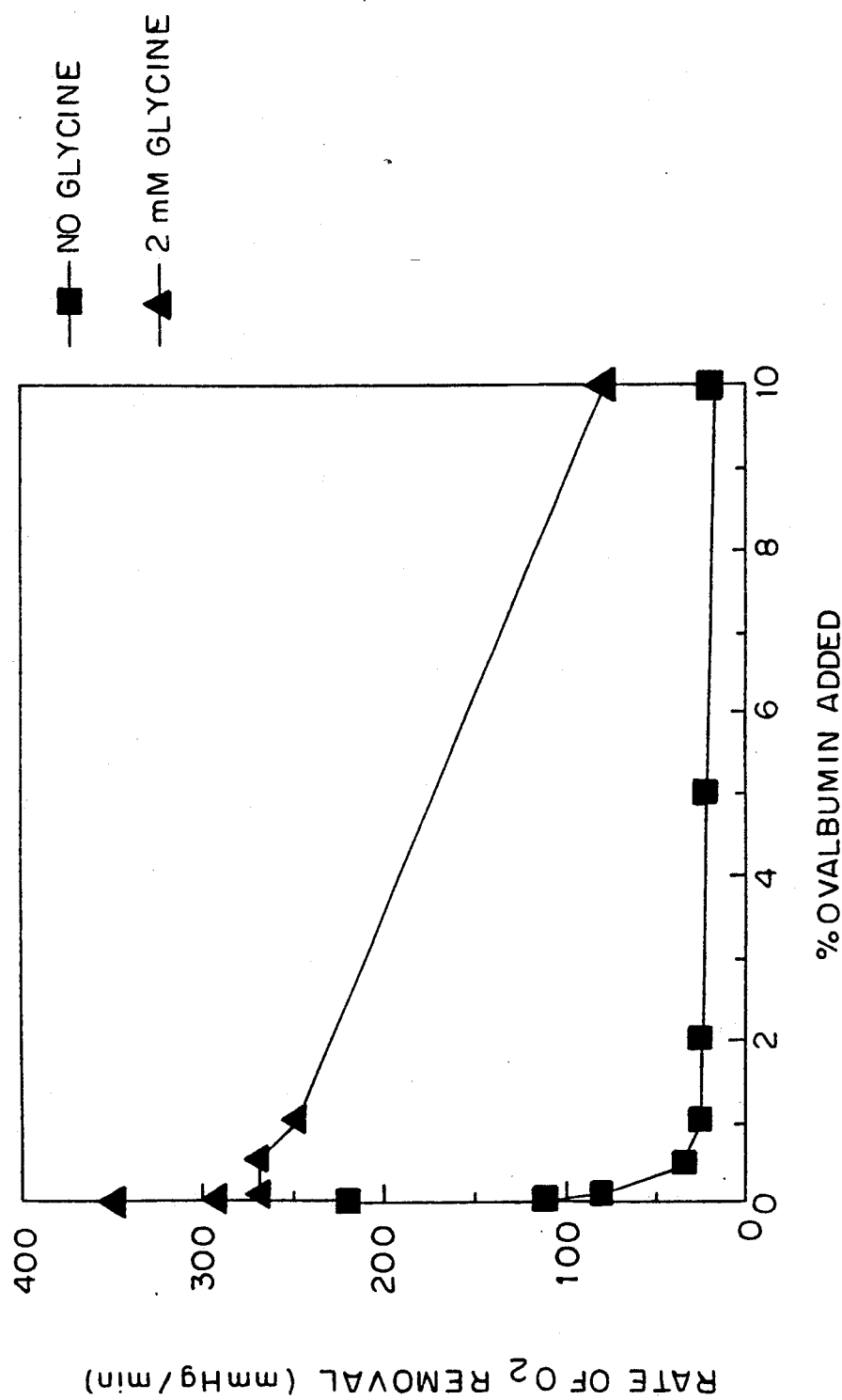

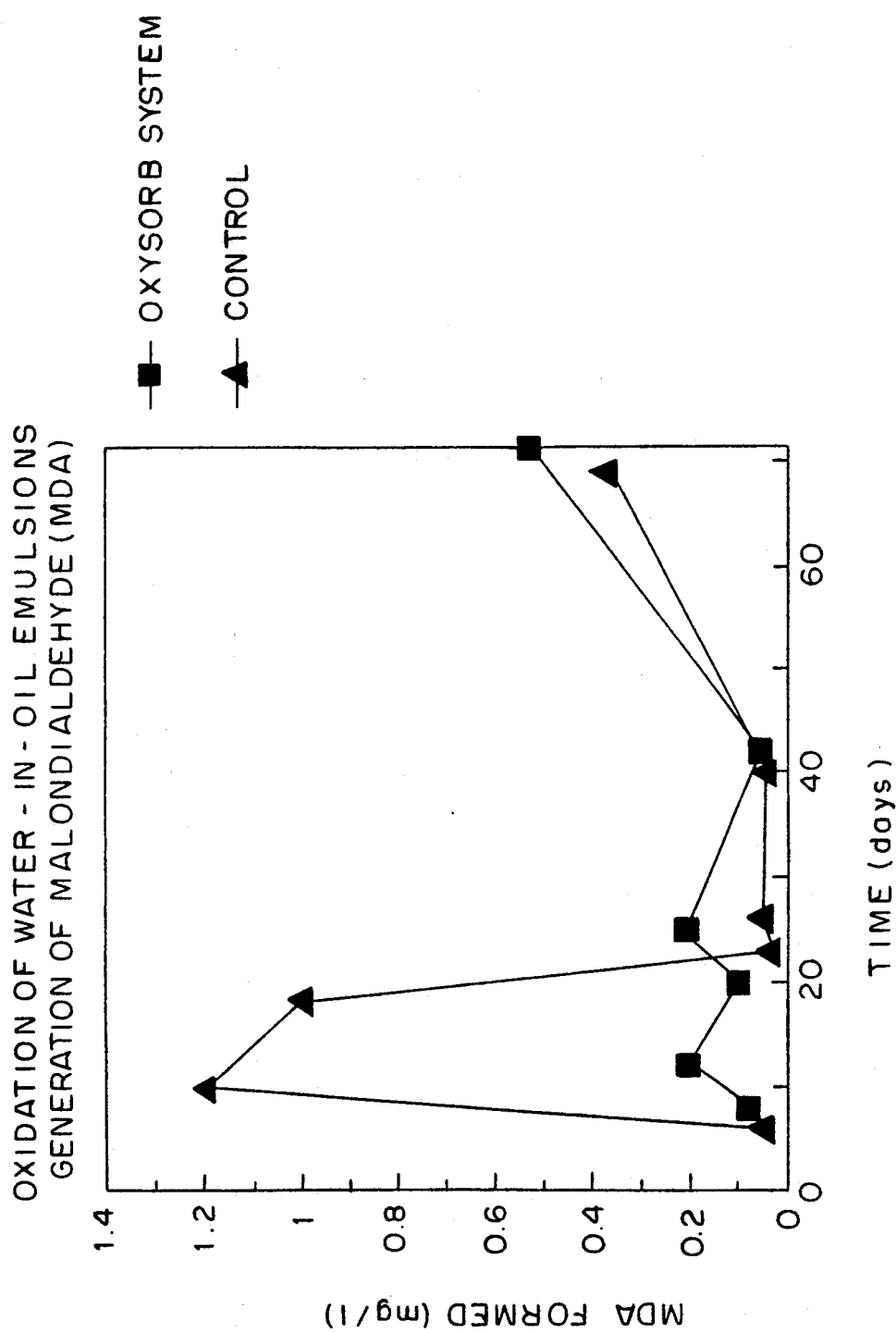

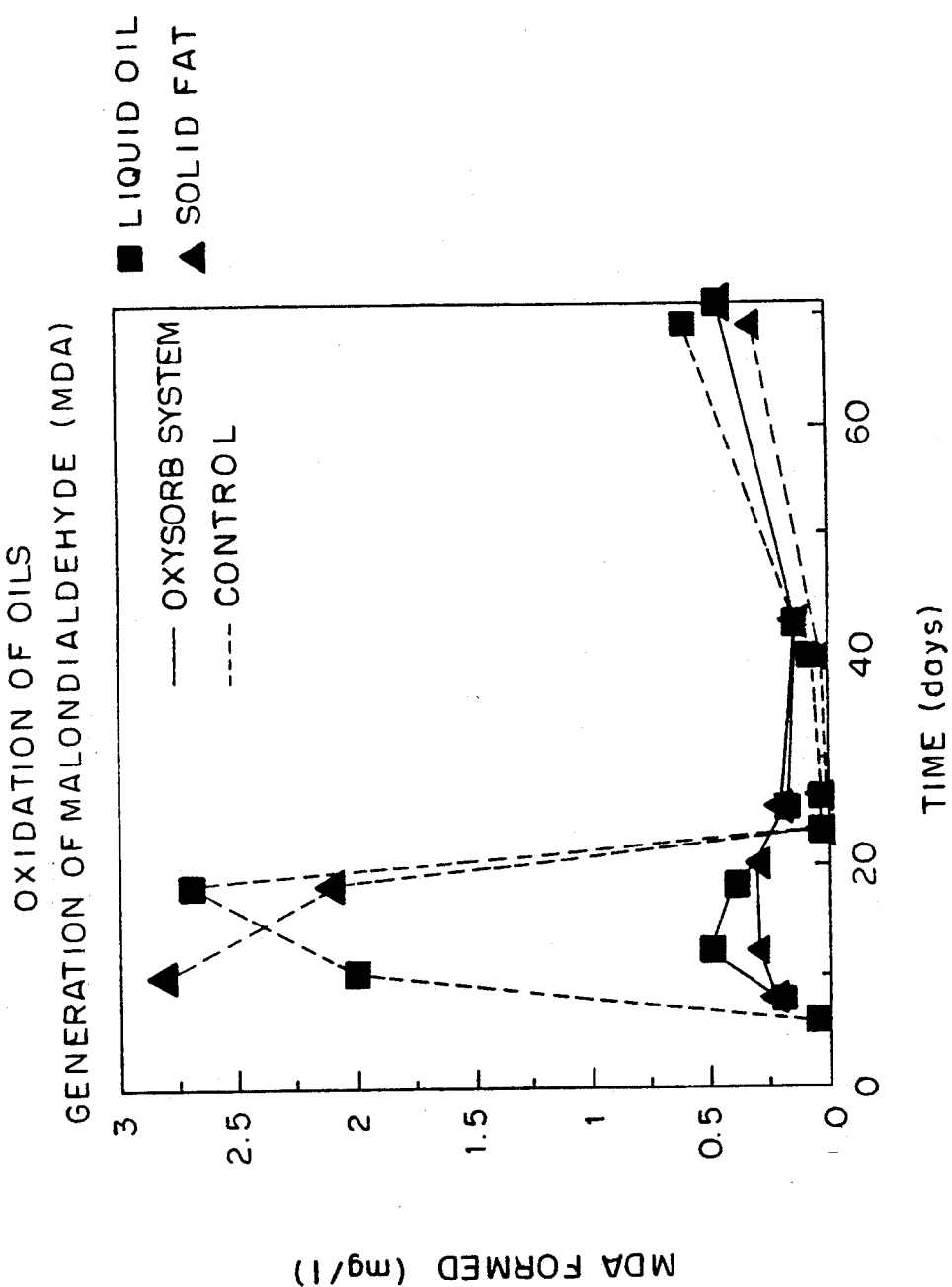

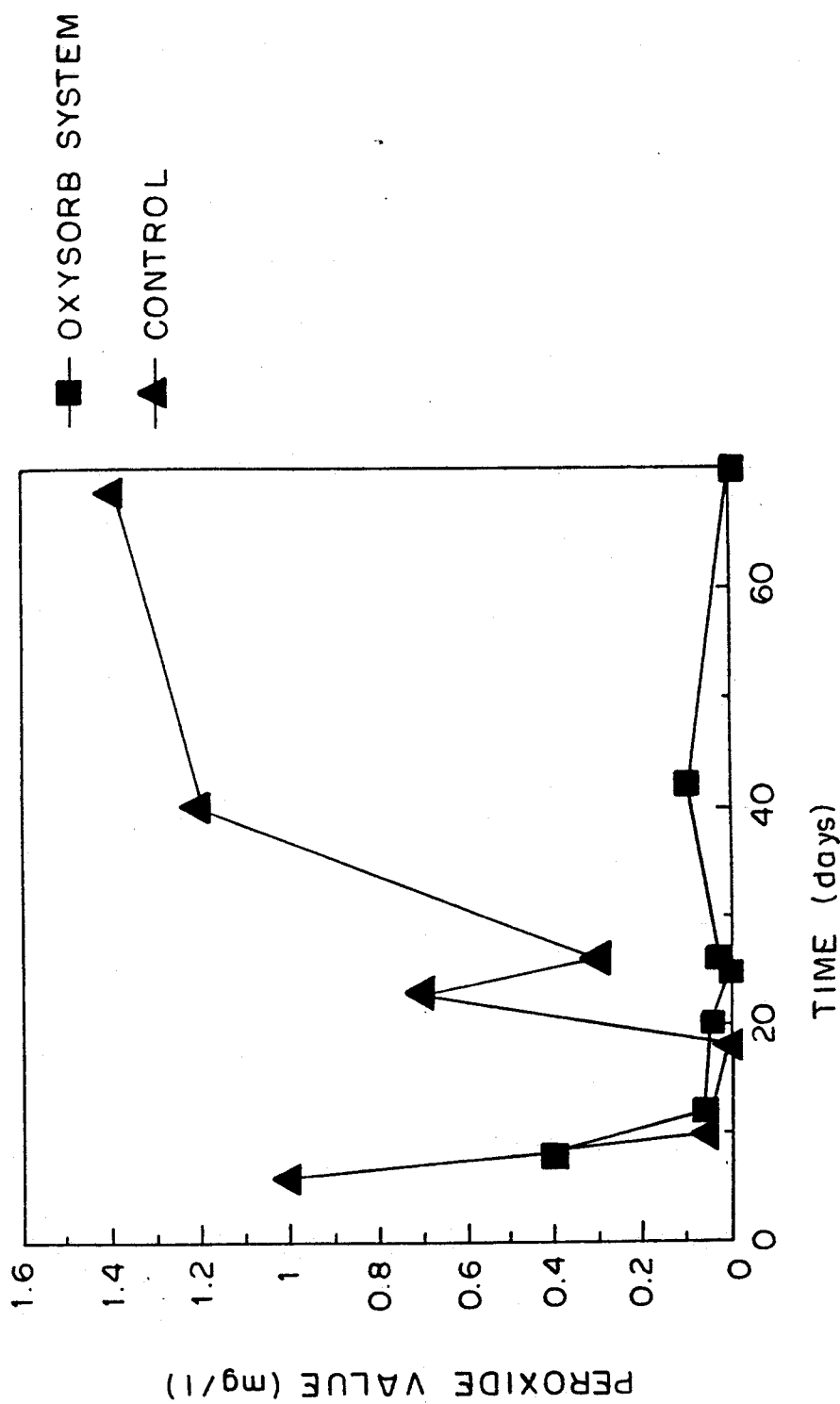

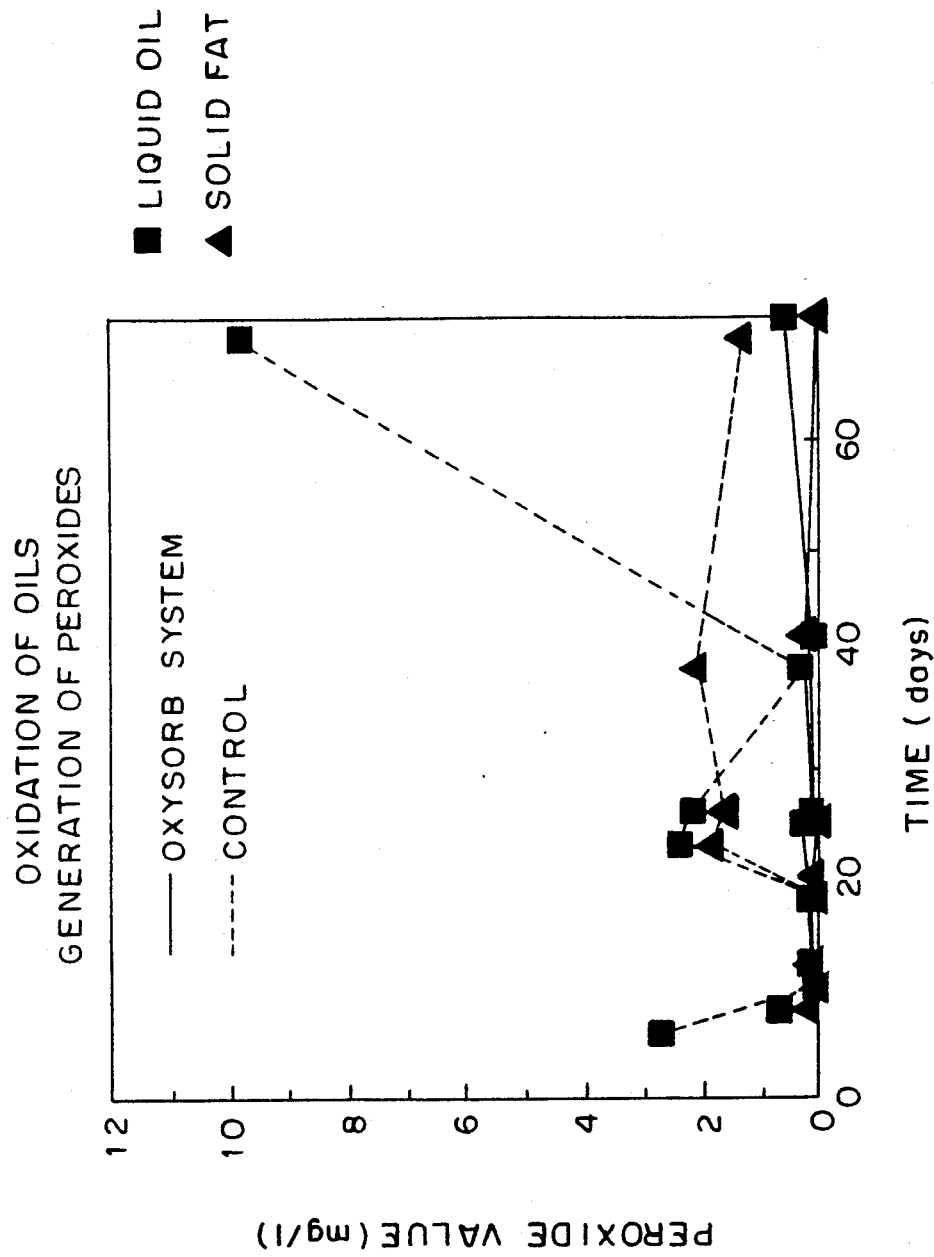

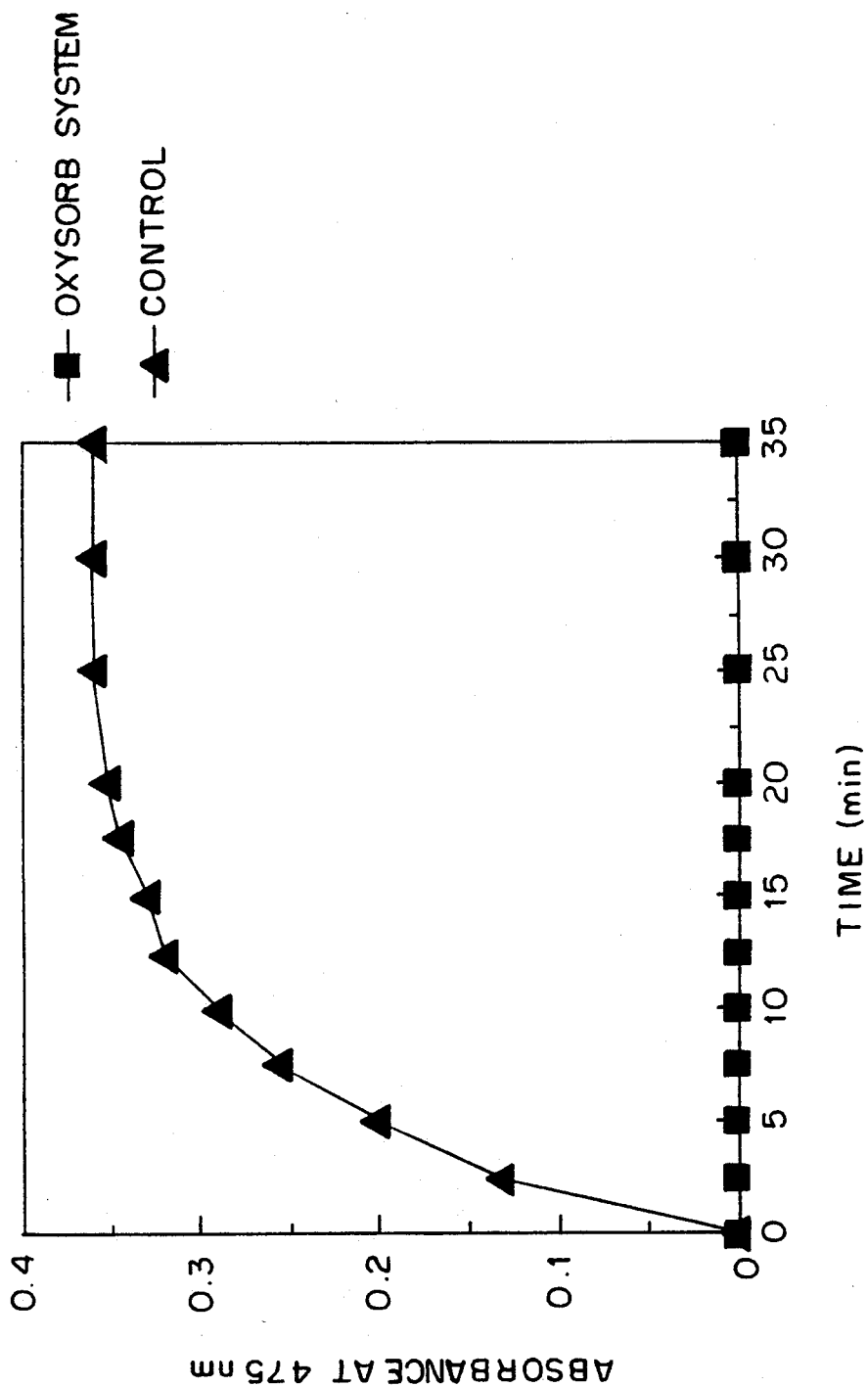

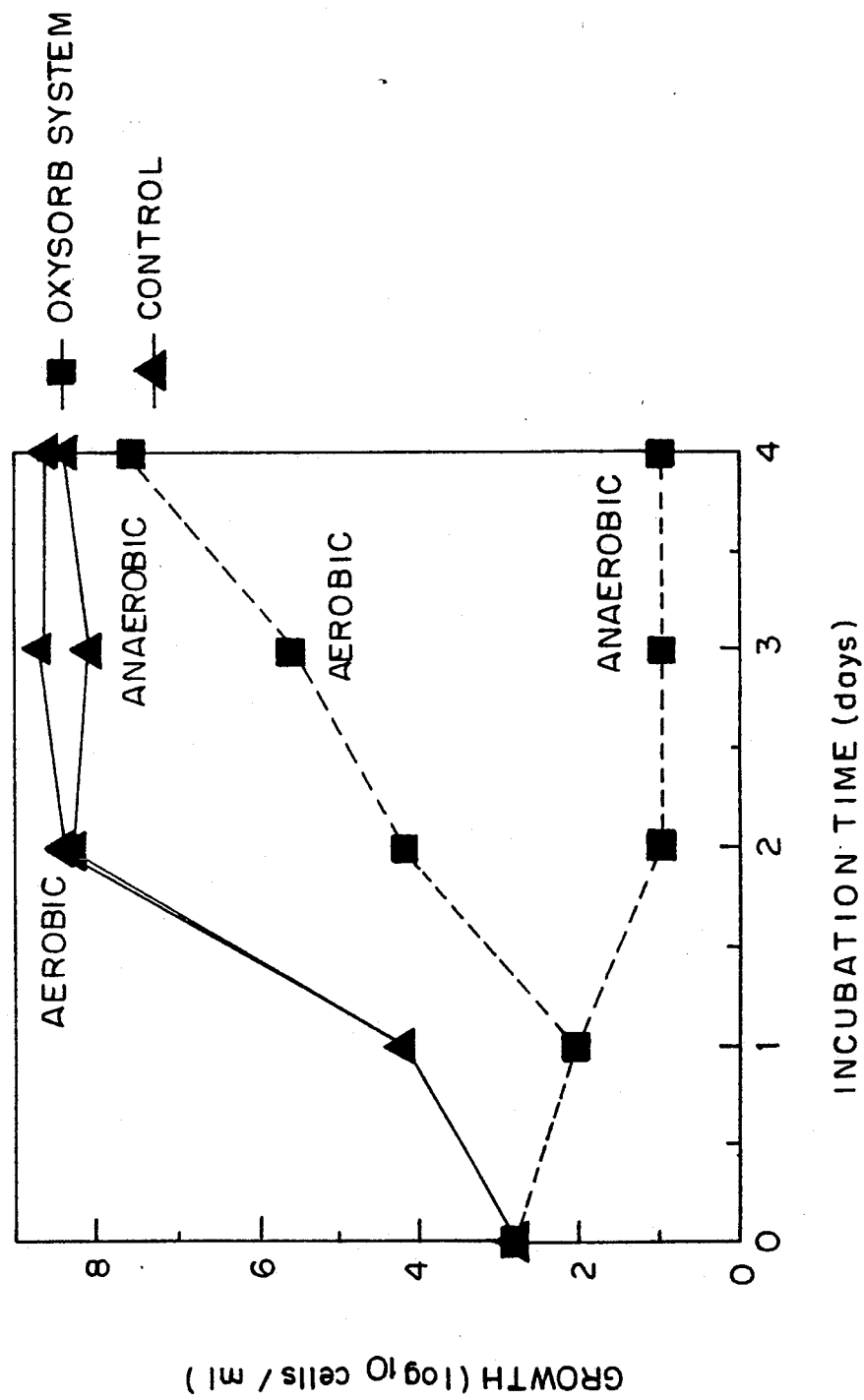

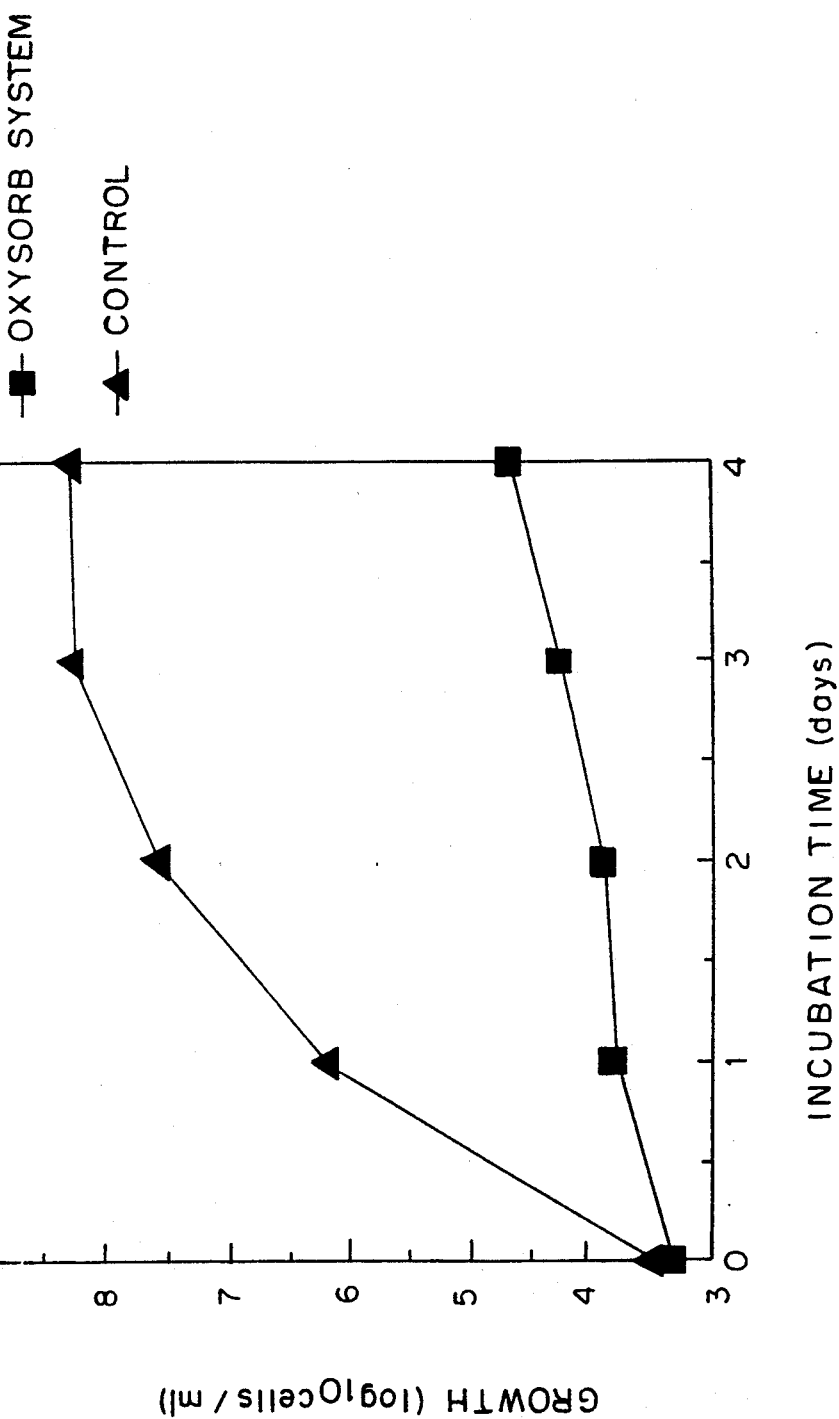

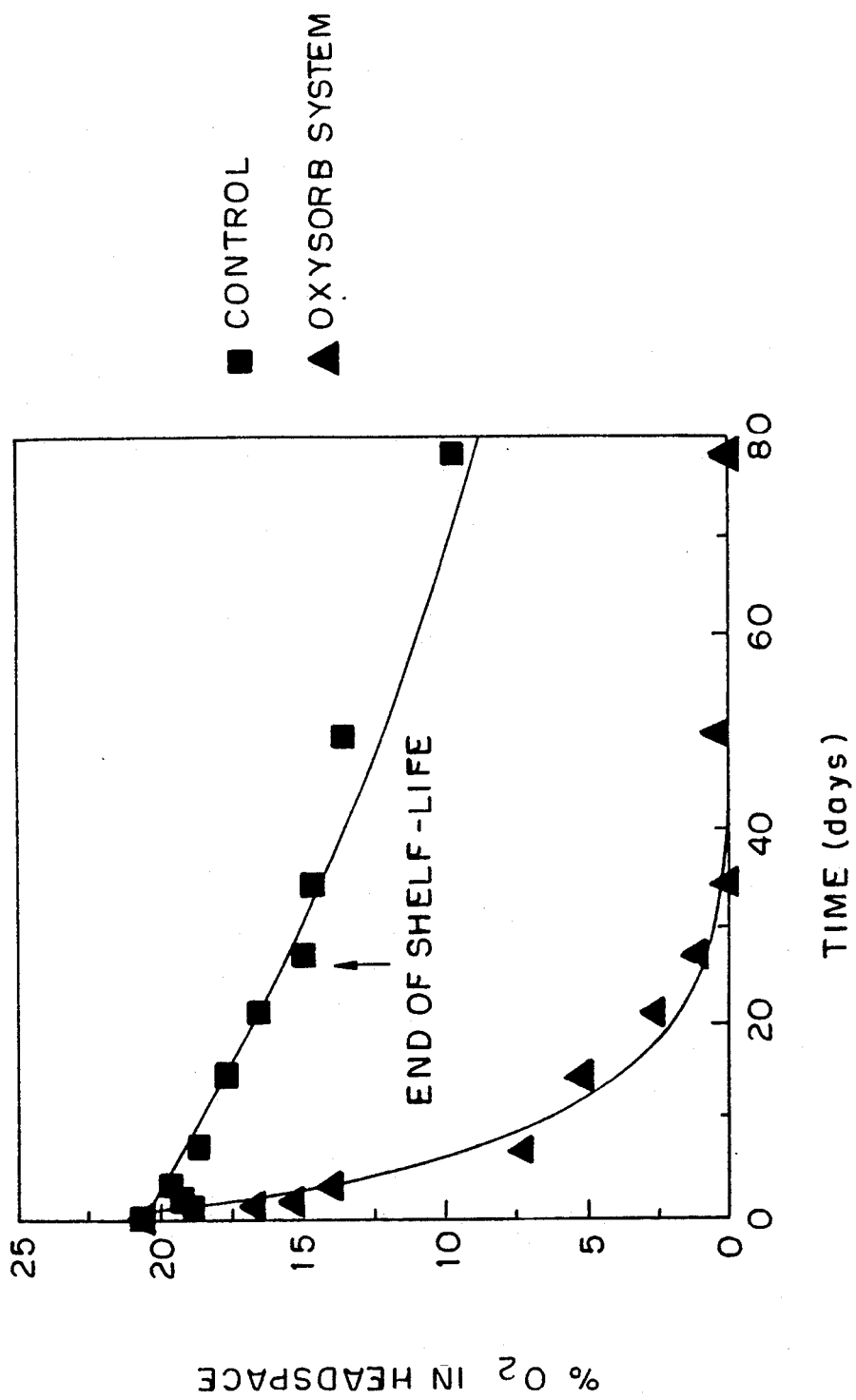

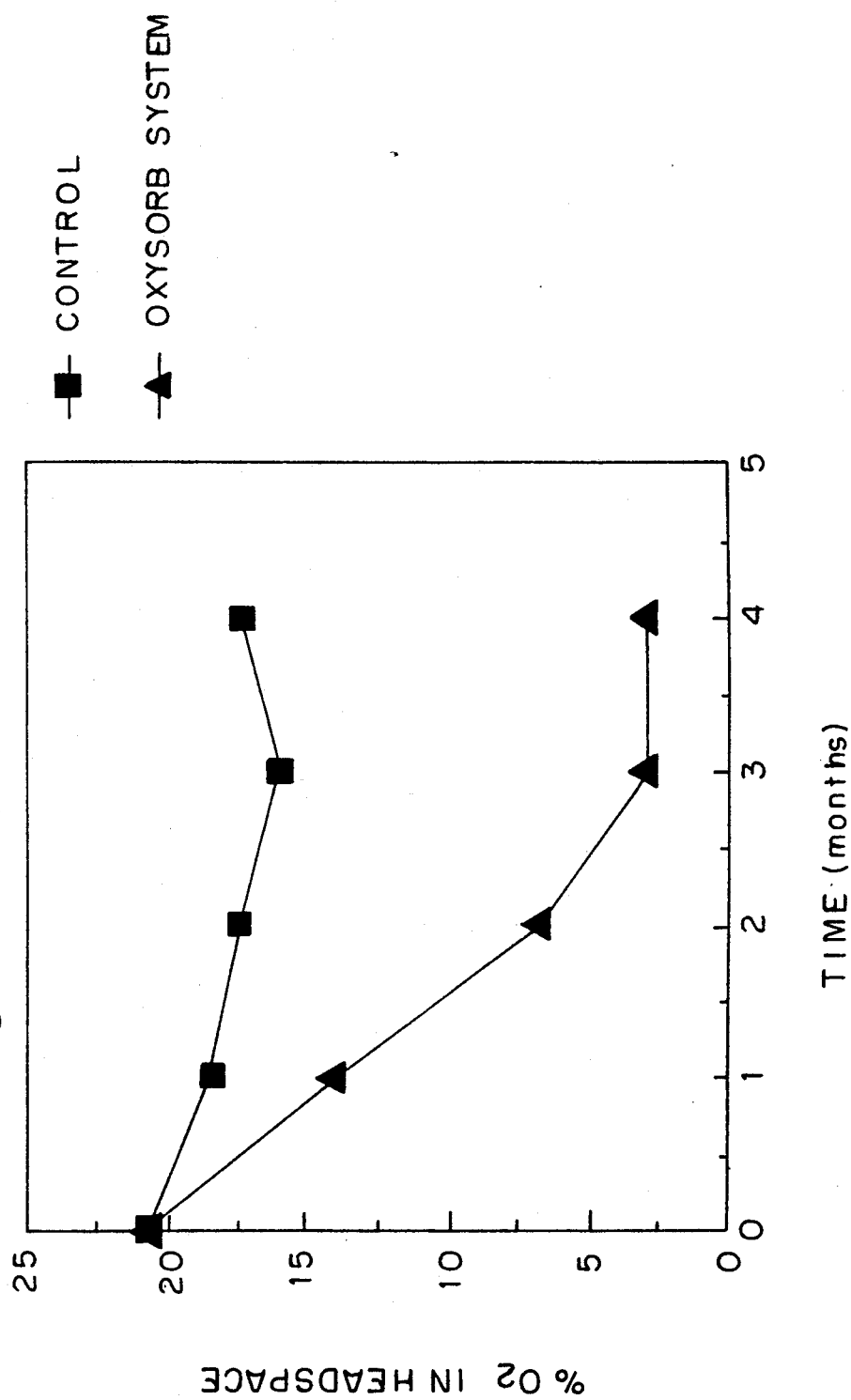

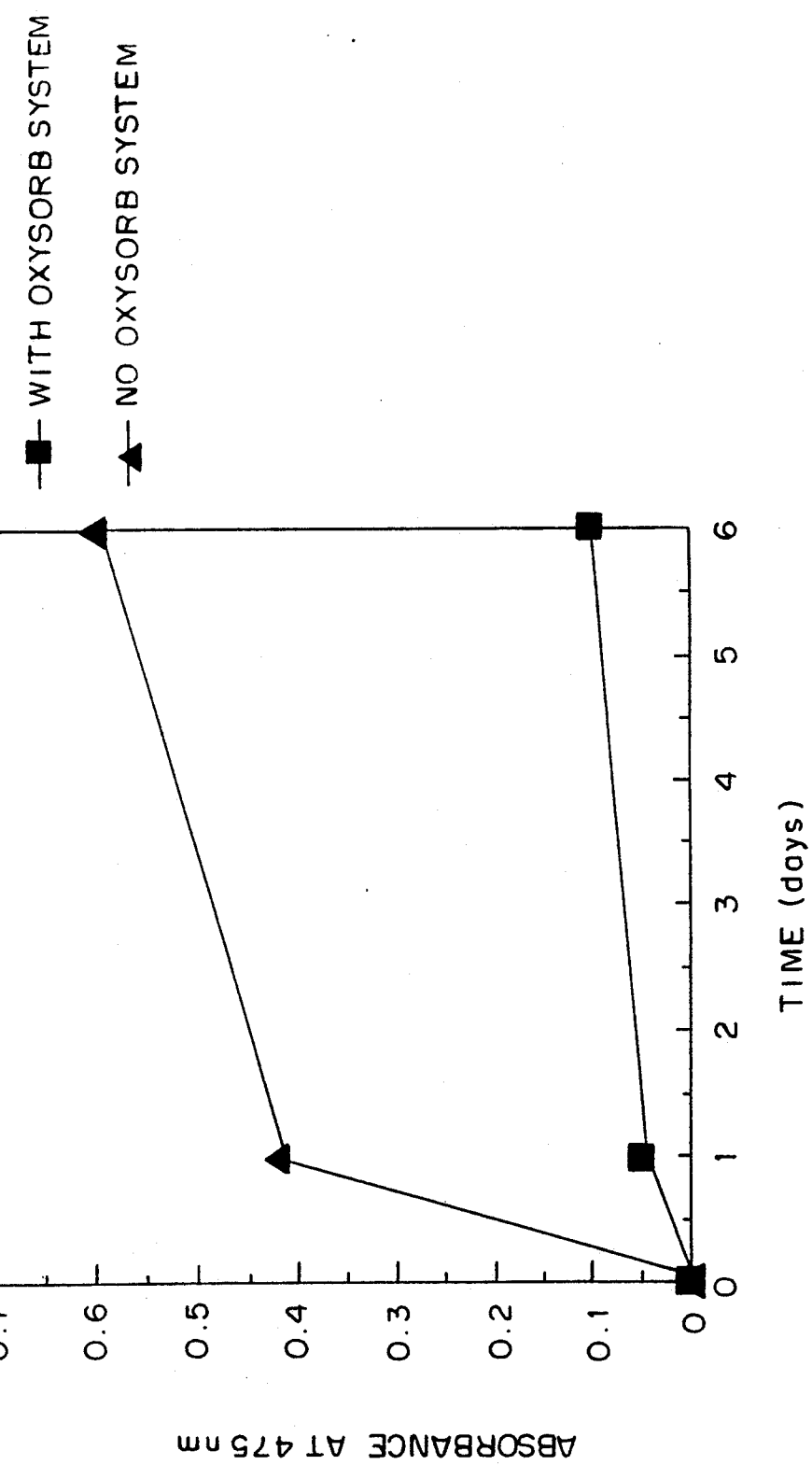

OXYGEN REMOVAL

CROSS-REFERENCE TO RELATED APPLICATIONS

This application is a continuation of application Ser. No. 07/279,604, filed Dec. 5, 1988, now abandoned, which was a continuation of application Ser. No. 07/100,971, filed Sep. 25, 1987, now abandoned.

FIELD OF THE INVENTION

The present invention relates to a process for removing oxygen from enclosed spaces.

BACKGROUND OF THE INVENTION

A change in the mechanism of food distribution has brought about an increasing demand for packaged foods. While packaged food is susceptible to deterioration in a variety of ways, depending upon conditions during distribution and storage, one of the most serious problems arises from spoilage due to oxygen. A wide variety of packaged foods are caused to deteriorate by oxidation since they are readily oxidizable. Oxidation causes changes in color and flavors, reduction in nutritional value, and other disagreeable conditions which give rise to complaints from consumers.

The changes in quality of packaged foods can also be caused by microorganisms. In order to prevent changes due to microorganisms or oxidation, it is customary to rely on food additives, such as antimicrobial and antimycotic agents and antioxidants.

Current methods for removing oxygen from packages are fraught with shortcomings:

1. Flushing with inert gases results in incomplete oxygen removal, particularly in the interior of porous foods. Furthermore, inert gas flushing provides no protection against subsequent oxygen influx. In order to flush with inert gases, the package interiors are evacuated and nitrogen or carbon dioxide gas is sealed in the evacuated package. Another problem with this method of preventing oxidative deterioration of foods is that an exact selection of combinations of articles to be packaged, and packaging material are required to achieve the intended results. Selection of favorable conditions for the methods demands a tremendous amount of time and data, and use of a high-efficiency packaging machine and a highly gas-impervious packaging material.

2. Vacuum packaging can only be used for certain foodstuffs, because some foodstuffs are likely to be deformed in the negatively pressurized interior of the package.

3. Coupled enzyme systems, such as glucose oxidase/peroxidase, undergo rapid inactivation and are very sensitive to changes in pH, water activity, solvent system, salt content, temperature, and various other factors. Additionally, these systems require the addition of water from the outside for their action, and therefore cannot be effectively used for low-water content foodstuffs, although they may work reasonably well with foodstuffs containing a great amount of water. These systems thus have limited practical utility.

4. Packages containing elemental iron remove oxygen by virtue of rusting, but at a very slow rate. Thus, this is impractical. This method is virtually ineffective below 0° C., and therefore provides no protection against common oxidative freezer damage.

5. The removal of oxygen by hydrogen gas is expensive and burdensome. The material to be protected is packaged in a material of a laminated structure of a polyester/metal foil/Surlyn/palladium/Surlyn (trademark of ionomer by DuPont Company) by gas substitution with a mixture of hydrogen and nitrogen gases whereby oxygen remaining in the package is reacted with the hydrogen gas under the catalytic action of palladium in the laminate to permit elimination of oxygen.

Addition of an antioxidant, antiseptic, or any other like additives to foodstuffs, which has been extensively adopted for the purposes of preservation, has the disadvantage that a technically sufficient amount of additives is prohibited by various statutes and regulations concerning additives for foodstuffs, pharmaceuticals, or cosmetics in light of their adverse effects on the human body. In addition, known hazardous materials cannot be used for foods, pharmaceuticals, and cosmetics.

The sensitivity of ascorbic acid to copper-catalyzed oxidation was recognized immediately after its discovery by Szent-Gyorgyi in 1928, and its structural determination and chemical synthesis in 1933. During the past 50+ years, a multitude of studies were conducted to investigate the kinetics and thermodynamics of oxidation of ascorbic acid by transition metals such as copper and iron, and their various chelates.

Historically, trace amounts of copper (less than 0.1 ppm) have been known to catalyze oxygen radical formation and lipid peroxidation, leading to rapid food spoilage, especially of food susceptible to oxidative damage. Therefore, painstaking efforts are being made in several food areas, such as the dairy industry, to eliminate all exposure of food to copper-containing equipment. Higher levels of copper are expected to aggravate this deteriorative effect of copper. Based on this current knowledge, the system of the present invention is not obvious and is contrary to conventional wisdom, since 5–7 ppm copper in the presence of a reducing agent, such as ascorbic acid, completely preserves oxygen-sensitive foods.

Nakamura et al., in U.S. Pat. No. 4,384,972, disclose an agent for maintaining the freshness of a packaged foodstuff comprising a salt of manganese (II), iron (II), cobalt (II), or nickel (II), an alkali compound, and a sulfite or deliquescent substance. Ascorbic acid or a salt thereof may optionally be included.

Siegel, in U.S. Pat. No. 3,320,046, discloses a formulation for conditioning cut flowers comprising an inorganic compound selected from the group consisting of water soluble inorganic salts or chelates which contain the one of the following metal ions: copper (II), zinc (II), manganese (II), cobalt (II), or nickel (II). The second component of the composition is ascorbic or isoascorbic acid, and the third component of the composition is an antioxidant such as a vinyl ether, an alkyl phenol, a phenolic ether, or the like.

Pottier, in U.S. Pat. No. 3,294,825, discloses an antioxidant composition for protecting lipids against oxidation comprising a combination of ascorbic acid and citric acid.

Stone, in U.S. Pat. No. 2,892,718, discloses a composition for treating malt beverages comprising sodium hydrosulfite and a salt of ascorbic acid.

Japanese patent 55-118344 discloses a method for preventing discoloration by immersing the vegetables in an aqueous solution containing an acid, a chelating agent such as sodium metaphosphate, and a harshness-removing agent such as burnt alum.

SUMMARY OF THE INVENTION

It is an object of the present invention to overcome the above-mentioned deficiencies in the prior art.

It is another object of the present invention to provide a system for reducing oxidative damage to packaged materials such as foods, pharmaceuticals, and cosmetics in a safe manner that does not affect the taste.

It is yet another object of the present invention to provide a system for preserving materials such as foodstuffs, pharmaceuticals, and cosmetics from microbial contamination.

The oxygen-removing composition of the present invention, also referred to as Oxysorb, comprises a combination of a reducing agent, from here on called an oxygen scavenger, and a small amount of a transition metal which can exist in two valence states, such as copper. The oxygen-removing system may be dissolved in or otherwise mixed thoroughly with the material to be protected from oxidation without producing any harmful effects, or it may be added in a small oxygen-permeable pouch containing the system and a suitable solvent.

The oxygen-absorbing system of the present invention protects some foods, ingestibles, and topical compositions against oxygen-mediated generation of off-flavors and odors, discoloration, enzymatic browning, loss of texture, syneresis, rheological changes, and growth of aerobic bacteria, yeasts, and molds. The system is effective at refrigerator, freezer, and room temperatures.

Oxygen removal occurs with any easily oxidizable reducing agent (oxygen scavenger) such as ascorbic acid. Hereinafter, the reducing agent will be exemplified by ascorbic acid. Most of these reactions are very slow and must be accelerated by light (as in the case of FMN or flavin mononucleotide) or by a transition metal capable of existing in 2 valence states. For exemplary purposes, the transition metal used is copper. The term copper denotes a species of copper which is soluble in the system in which it is used, preferably salts of $Cu^+$ or $Cu^{2+}$. Therefore, copper functions as a catalyst, cycling between $Cu^+$ and $Cu^{2+}$, while never being consumed. The reducing agent, however, is used up and therefore determines the total oxygen depletion capacity.

Although many transition metals catalyze this reaction, copper is the preferred substance in foods, since it effects oxygen removal without the concomitant generation of highly reactive oxygen radicals. Many other metals in the presence of ascorbic acid promote lipid peroxidation and food deterioration. However, they may still be added to foods when contained within a pouch (see below). In addition to completely preserving the color, flavor and texture of foods, $Cu^{2+}$-ascorbate also inhibits the growth of aerobic microorganisms presumably by forming hypochlorous acid (HOCl). Other metals tested fail to produce this compound and exhibit no measurable bactericidal effects.

The removal of oxygen by the system of the present invention can be described as follows, with ascorbic acid (AA) given as the example of the oxygen scavenger:

Ascorbic acid, vitamin C, reduces $Cu^{2+}$ to $Cu^+$ to form dehydroascorbic acid (equation I). Cuprous ions ($Cu^+$) form a complex with oxygen, and an electron transfer occurs to give cupric ions ($Cu^{2+}$) and superoxide anion radicals (equation II). In the presence of copper, the latter radicals rapidly disproportionate to oxygen and hydrogen peroxide (equation III). The complex of copper-ascorbate rapidly reduces the hydrogen peroxide to water (equation IV), without the concomitant generation of hydroxyl radical (equation VI), a highly reactive oxidant. The net reaction (equation V) effects complete oxygen removal from an aqueous solution within 3 minutes as shown in FIG. 1.

$$AA + 2Cu^{2+} \longrightarrow DHAA + 2Cu^+ + 2H^+ \quad (I)$$

$$2Cu^+ + 2O_2 \longrightarrow 2Cu^{2+} + 2O_2^- \quad (II)$$

$$2O_2^- + 2H^+ + Cu^{2+} \longrightarrow O_2 + H_2O_2 + Cu^{2+} \quad (III)$$

$$H_2O_2 + Cu^{2+} - AA \longrightarrow Cu^{2+} - DHAA + 2H_2O \quad (IV)$$

Net reaction:

$$AA + 1/2 O_2 \longrightarrow DHAA + H_2O \quad (V)$$

where DHAA = droascorbic acid.

This reaction mechanism has been deduced from the following lines of experimental evidence:

The generation of superoxide anion radical ($O_2^-$) by equation II has been demonstrated by the substantial acceleration of ascorbic acid oxidation by superoxide dismutase (FIG. 2), an enzyme that catalyzes equation III. By disproportionating $O_2^-$ to $H_2O_2$ and $O_2$ this enzyme increases the steady-state concentration of $H_2O_2$, which then oxidizes ascorbic acid. Similarly, inhibition by catalase (FIG. 2), an enzyme that catalyzes equation VII, confirms the formation of $H_2O_2$ during the removal of oxygen by the system of the present invention. If there were no hydrogen peroxide generated during reaction V, this enzyme would have no effect.

In past studies, $Cu^{2+}$ has been found to exhibit some superoxide dismutase activity, i.e., it catalyzes the conversion of superoxide anion radical to hydrogen peroxide, whereas $Fe^{3+}$ lacks this effect. This difference partly explains why copper is the preferred metal for Oxysorb used in solution in edible systems, because the superoxide anion radical is another potentially dangerous activated oxygen species.

Hydrogen peroxide is very stable, even in the presence of $Cu^{2+}$ (result not shown). $Cu^{2+}$-ascorbate, however, degrades hydrogen peroxide very rapidly, as shown by the large stimulatory effect of $H_2O_2$ on the oxidation of $Cu^{2+}$-ascorbate (FIG. 3). Thus, $Cu^{2+}$-ascorbate rapidly reduces hydrogen peroxide to water (equation IV) without the concomitant production of hydroxyl radical (equation VI) or oxygen (equation VII). No generation of $O_2^-$ or .OH could be detected under a variety of conditions.

$$H_2O_2 + Cu^+ \rightarrow .OH + OH^- + Cu^{2+} \quad (VI)$$

$$H_2O_2 + Cu^{2+} \rightarrow H_2O + \tfrac{1}{2}O_2 + Cu^{2+} \quad (VII)$$

The system of the present invention has been found to rapidly remove hydrogen peroxide, a potentially dangerous oxidant generated in the above reactions. $Fe^{3+}$-ascorbate removes hydrogen peroxide much more slowly than the system of the present invention (FIG. 4). In addition to reducing $H_2O_2$ to water by equation IV, $Fe^{3+}$-ascorbate also produces a small amount of hydroxyl radical by the Fenton reaction (equation VIII) as shown in FIG. 5.

$$H_2O_2 + Fe^{2+} \rightarrow OH^- + \cdot OH + Fe^{3+} \quad \text{(VIII)}$$

To summarize, the removal of oxygen by the system of the present invention produces an intermediate which is rapidly reduced by copper ascorbate.

The presence of copper in the Oxysorb system produces no hydroxyl radical, a very potent and indiscriminate oxidant, whereas iron does produce this radical, cf. equation VIII.

$Cu^{2+}$ catalyzes the reduction of the superoxide anion radical to hydrogen peroxide, whereas iron does not.

The advantage of the Oxysorb system is that the oxygen is rapidly removed without the production of any radicals.

The copper in the Oxysorb system functions as a catalyst in reducing oxygen to $O_2^-$ (equation II), and then catalyzing the reduction of $O_2^-$ to hydrogen peroxide (equation III). Copper-ascorbate catalyzes the reduction of hydrogen peroxide to water (equation IV). The amount of ascorbic acid determines the total oxygen removing capacity. Ascorbate reduces $Cu^{2+}$ to $Cu^+$ (equation I), reduces hydrogen peroxide to water (equation IV), and scavenges and inactivates any potential radicals in the food system.

Conventional wisdom dictates keeping even trace amounts of copper away from any oxygen-sensitive material, since copper is an excellent catalyst for free radical generation, lipid peroxidation, and subsequent putrefaction of foods. However, the system of the present invention does not appear to adhere to conventional wisdom for several reasons:

1. Oxygen is absent during most of the shelf-life of the food, since it is rapidly depleted by the system of the present invention immediately after the components are mixed. Oxygen amounts exceeding the capacity of the system should be avoided by reducing the headspace or partially flushing with an inert gas. Otherwise $O_2$ and $Cu^{2+}$ (in the absence of any remaining ascorbic acid) will cause food spoilage.

2. The relatively high concentration of copper used in the invention (~5 ppm) catalyzes the rapid reduction of $O_2^-$ to $H_2O_2$.

3. The relatively high concentration of copper used in the invention (around 5 ppm) catalyzes the rapid breakdown of hydrogen peroxide to form water, which is inert.

In addition to inhibiting oxidative rancidity and other oxygen-mediated deteriorative reactions, the system of the present invention also appears to reduce spoilage by suppressing growth of aerobic microorganisms, both through oxygen deprivation and direct bactericidal action.

BRIEF DESCRIPTION OF THE DRAWINGS

FIG. 17 shows the Arrhenius plot of copper-mediated oxygen utilization. The initial rates were determined in 50 micromolar copper sulfate, 1 mM sodium ascorbate, and 50 mM Tris, pH 7.4 at 10° C., 15° C., 20° C., 25° C., 30° C., 35° C., and 40° C.

FIG. 18 shows the effect of chelating agents on oxygen removal by Oxysorb. The rate of $O_2$ consumption at 25° C. in 10 mM sodium ascorbate, 100 micromolar copper gluconate, 50 mM Tris, pH 7.4, and 1 mM chelating agent was monitored using a Clark electrode.

FIG. 19 shows the effect of different transition metals on oxygen removal. The rate of $O_2$ consumption at 25° C. in 10 mM sodium ascorbate, 50 mM Tris, pH 7.4, and 100 micromolar transition metal was monitored using a Clark electrode.

FIG. 20 shows the effect of different reducing agents on copper-mediated oxygen removal. The rate of $O_2$ consumption at 25° C. in 100 micromolar copper gluconate, 50 mM Tris, pH 7.4, and 1 mM reducing agent was monitored using a Clark electrode.

FIG. 21 shows the effect of protein on $O_2$ removal by Oxysorb. Increasing amounts of ovalbumin in the absence and presence of glycine were added to the Oxysorb system and the rate of $O_2$ consumption at 25° C. was monitored using a Clark electrode.

FIG. 22 shows the effect of Oxysorb on the oxidation of emulsions. Samples were stored in oxygen impermeable plastic jars at room temperature and analyzed intermittently for malondialdehyde (MDA).

FIG. 23 shows the effect of Oxysorb on the oxidation of oils. Samples were stored in oxygen impermeable plastic jars at room temperature and analyzed intermittently for malondialdehyde (MDA).

FIG. 24 shows the effect of Oxysorb on the oxidation of emulsions. Samples were stored in oxygen impermeable plastic jars at room temperature and analyzed intermittently for lipid peroxidation.

FIG. 25 shows the effect of Oxysorb on the oxidation of oils. Samples were stored in oxygen impermeable plastic jars at room temperature and analyzed intermittently for lipid peroxidation.

FIG. 26 shows the effect of Oxysorb on polyphenol oxidase activity. The oxidation of 0.3 mg/ml DOPA by 0.02 mg/ml polyphenol oxidase at 30° C. in the absence and presence of 40 ppm copper gluconate / 0.2% ascorbic aid was monitored spectrophotometrically.

FIG. 27 shows the effect of 0.004% copper gluconate and 0.2% sodium ascorbate on the growth of E. coli at 25° C. under aerobic and anaerobic conditions.

FIG. 28 shows the effect of the oxygen scavenging system (0.004% copper gluconate and 0.2% sodium ascorbate) on yeast growth at 25° C.

FIG. 29 shows the effect of 0.004% copper gluconate and 0.2% sodium ascorbate on oxygen depletion in the headspace of Mexican salsas. The solid lines represent theoretical oxygen utilization rates calculated form first order kinetic parameters. All products were stored at 5° C.

FIG. 30 shows the effect of Oxysorb on $O_2$ removal from the headspace of pizza sauce stored at −12° C. Shredded cheese was dispersed in the sauce to increase its susceptibility to oxidative discoloration.

FIG. 31 shows the dependence of browning of potato water on Oxysorb (0.1% ascorbic acid and 0.004% copper gluconate) at 5° C.

DETAILED DESCRIPTION OF THE INVENTION

Figure 1:
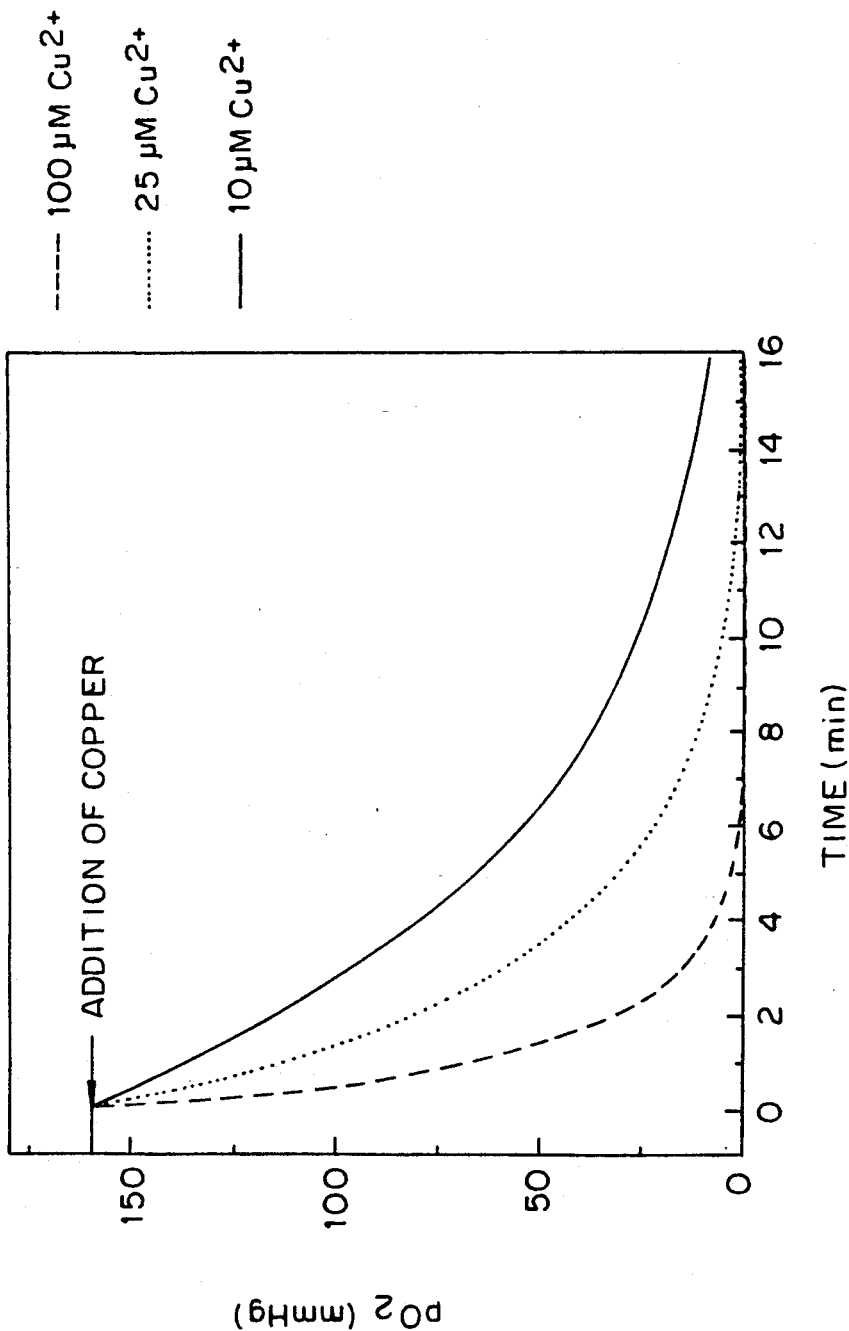
FIG. 1 shows the oxygen utilization by the copper-ascorbate oxygen scavenger system. The oxygen tension was measured in 1 mM sodium ascorbate and 50 mM Tris, pH 7.4 at 25° C. using a Clark oxygen electrode.
Figure 2:
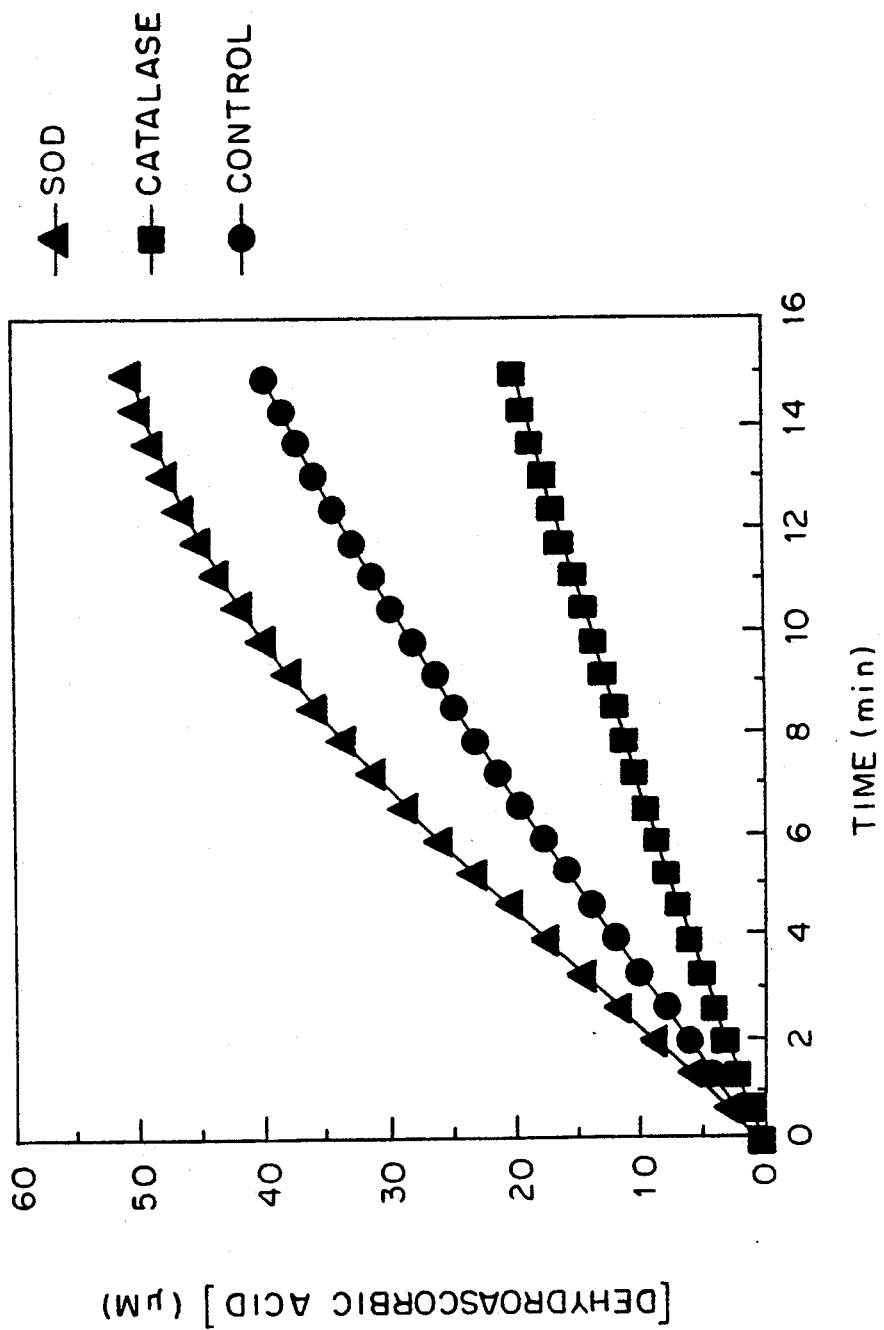
FIG. 2 shows the effects of 1000 U/ml catalase and 25 U/ml superoxide dismutase (SOD) on the oxidation of 50 micromolar ascorbic acid to dehydroascorbic acid in the presence of 1 micromolar $Cu^{2+}$. The rate of oxidation at 25° C. in 50 mM Tris, pH 7.4, was monitored spectrophotometrically.
Figure 3:
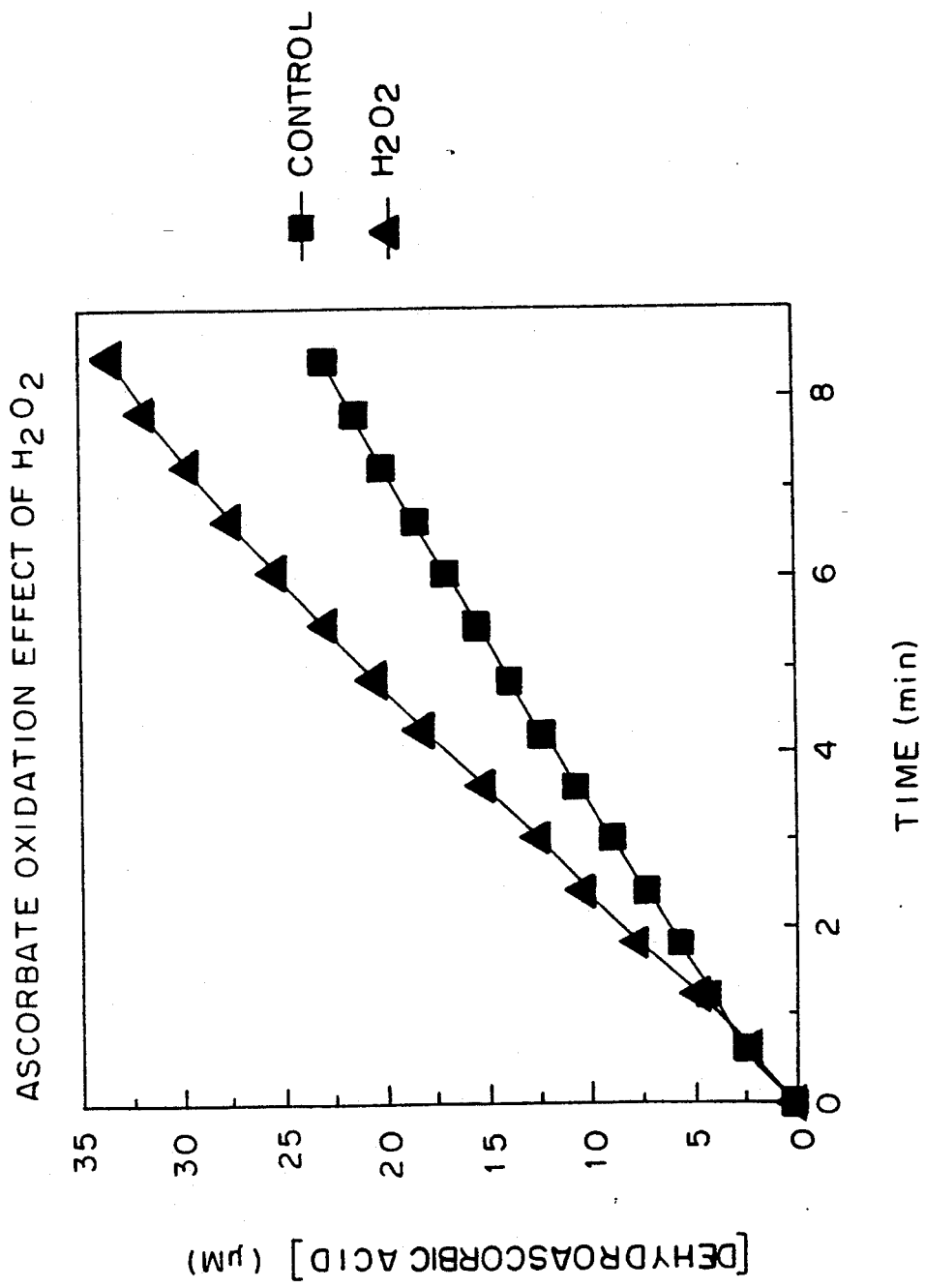
FIG. 3 shows the effect of 100 micromolar $H_2O_2$ on the oxidation of 50 micromolar ascorbic acid to dehydroascorbic acid in the presence of 1 micromolar $Cu^{2+}$. The rate of oxidation at 25° C. in 50 mM Tris, pH 7.4, was monitored spectrophotometrically.
Figure 4:
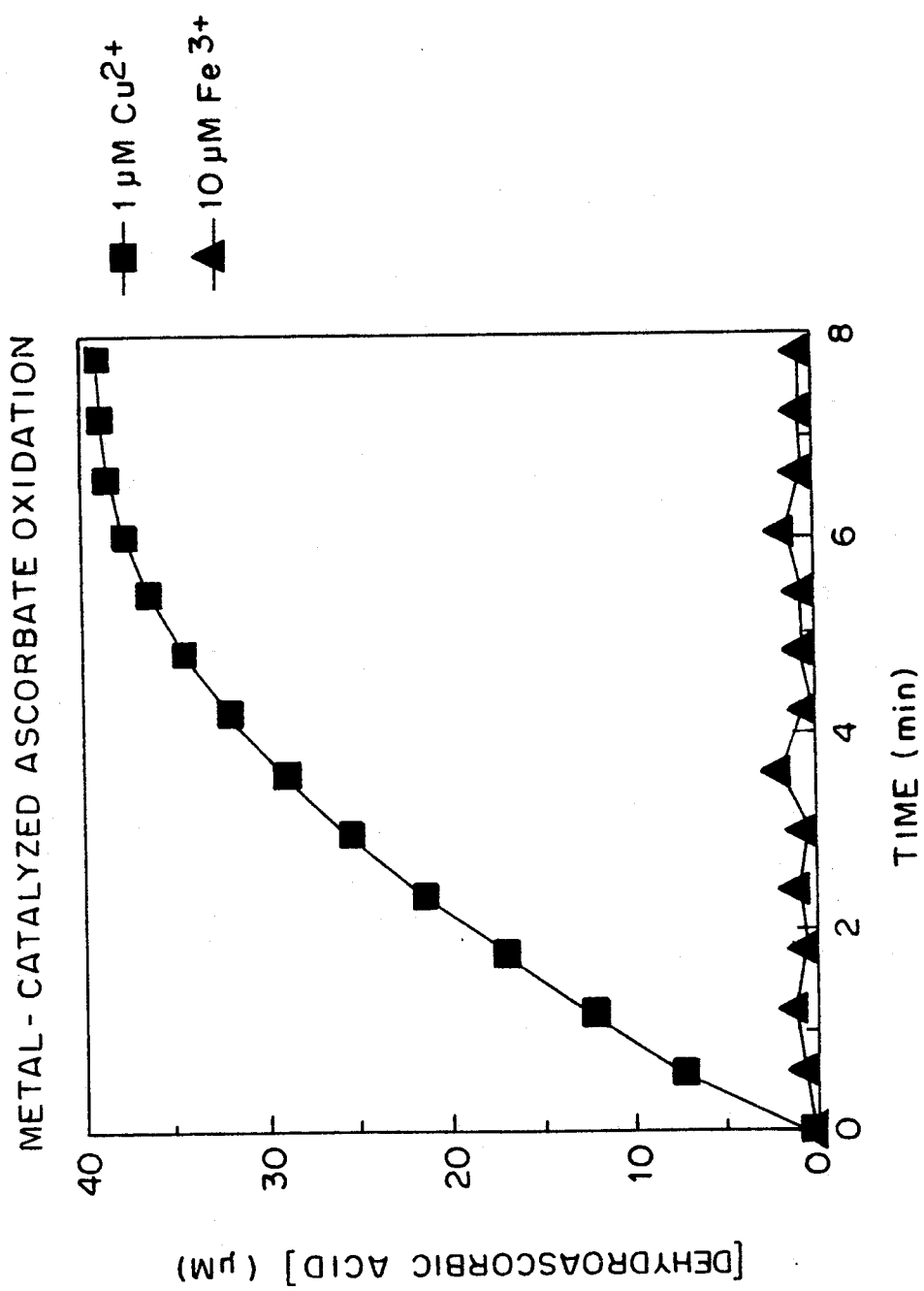
FIG. 4 shows the effects of 1 micromolar $Cu^{2+}$ and 10 micromolar $Fe^{3+}$ on the oxidation of 50 micromolar ascorbic acid. Both reactions were carried out at 25° C. in 50 mM Tris, pH 7.4.
Figure 5:
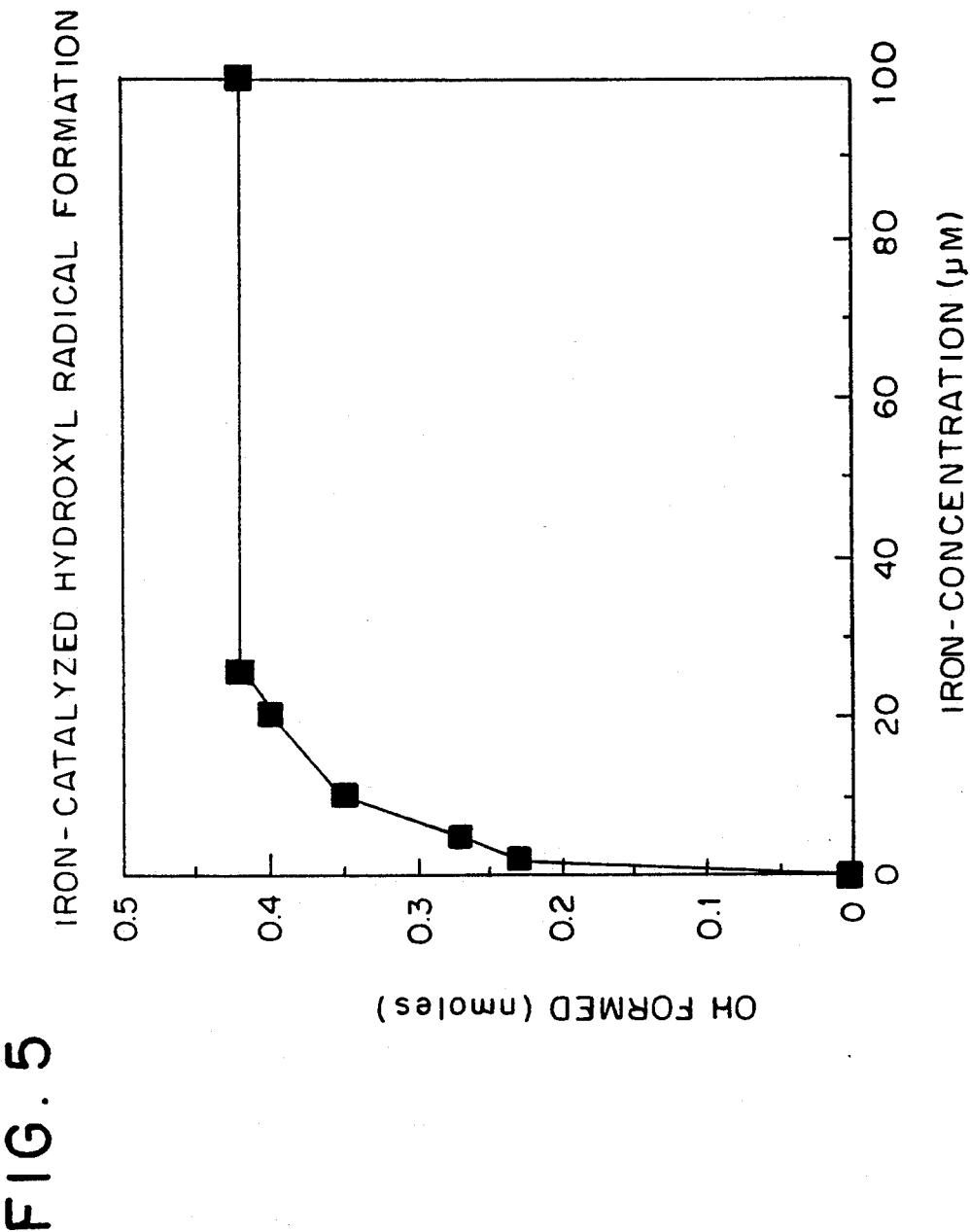
FIG. 5 shows the effect of $Fe^{3+}$ on the generation of hydroxyl radical (.OH) at 25° C. in 50 mM Tris, pH 7.4, 2 mM $H_2O_2$, 2 mM ascorbic acid and 50 mM DMSO. Hydroxyl radical was determined by quantitating formaldehyde formed from the reaction between .OH and DMSO.

The Oxysorb system of the present invention may be added directly to a food product which is to be preserved, or may be added to a food product in an oxygen-permeable pouch.

The total capacity for oxygen removal is determined by the amount of ascorbic acid. The complete 2-step reduction of 1 mole of oxygen to water requires 2 moles of ascorbic acid. This stoichiometry may be translated into the following equalities:

| 1 liter of air at 20° C. | = | 18.75 mmoles ascorbate |
|---|---|---|
| 1 liter of water at 20° C. | = | 0.50 mmoles ascorbate |
| | = | 0.099 g sodium ascorbate |
| | = | 0.01% sodium ascorbate in water |

For the above calculations we assumed an oxygen solubility of 0.25 mM in water at 20° C.; this was the experimentally determined oxygen solubility in 50 mM Tris, pH 7.4 at 20° C. The exact requirement for ascorbic acid in a food system will depend on the oxygen solubility in that particular solution or solid.

The total oxygen depletion capacity of the oxygen absorbing system is directly proportional to the amount of reducing agent in the system. The minimum concentration of reducing agent should be calculated for each application. An excess of reducing agent such as ascorbic acid merely provides longer protection, and has no detrimental effect on the food system.

The total amount of ascorbic acid or other reducing agent required to provide full protection throughout the shelf life of a packaged product may be substantially increased for the following five reasons:

1. If it is necessary to heat process the substrate during its manufacture, after the copper and the oxygen scavenger have already been added, significant amounts of the oxygen scavenger may become degraded.

2. A slow influx of oxygen into the system over a period of time will require more oxygen scavenger for full protection. For example, in the case of oxygen-permeable packaging materials, oxygen will slowly be added to the system from outside of the package.

3. The oxygen scavenger in the system not only reduces the copper from one oxidative state to another, but it also scavenges any deleterious oxygen radicals. Since both reactions oxidize ascorbic acid, a slight excess of ascorbic acid is required to provide sufficient radical scavenging antioxidant activity.

4. As ascorbic acid approaches its depletion, the rate of reduction of the metal becomes greatly depressed, since the concentration of ascorbic acid becomes rate-limiting. An excess of ascorbic acid assures rapid oxygen removal even at low oxygen concentrations.

5. Strong oxidizing agents added to certain foods may oxidize a portion of the oxygen scavenger, such as azodicarbonamide or bromate added to flour doughs.

Exposure of the Oxysorb system to oxygen and heat processing should be minimized in order to avoid extensive oxidation of the oxygen scavenger.

With the Oxysorb system of the present invention, oxygen is removed so as to prevent deleterious oxidation. This can be determined by standard testing methods, e.g., organoleptically in foods.

The system of the present invention can be introduced into the product to be preserved in a variety of ways. Of course, if the product to be preserved is a liquid, the system can be added directly to the liquid. In the case of a solid product, the system can be contained inside a pouch contained in the package of the product. The system may also be incorporated into the lid of a can or a jar, or incorporated into the wrapping material for the product. Alternatively, the dry metal/ascorbate powder can be enrobed in an oxygen-and water-permeable material. Another method is incorporation of the metal into the packaging material and addition of the oxygen scavenger to the product. This combination assures maximum stability of the system without compromising the speed of dissolved oxygen removal.

A particularly convenient method for incorporating the system of the present invention into a packaged product is by use of a pouch within the package. The metal/scavenger system is dissolved in a small volume of water inside a pouch consisting of a water-impermeable film with a high oxygen diffusivity. The pouch can then be added to the package to cause oxygen depletion.

An alternate version of the pouch contains compartments which are separated by a weak wall. One of the compartments contains the oxygen scavenger, and the other contains the metal salt, water, and propylene glycol or other carrier. Upon breaking the wall between the two compartments, the reactants mix and begin removal of oxygen. This compartmentalized design has the advantage of rendering the pouch itself shelf-stable in a high oxygen environment for years, until it becomes mechanically activated by breaking the seal by light compression. The only disadvantage of this configuration is the relatively slow dissolution of the reactants.

When the oxygen absorbing system of the present invention is used in a two-compartment pouch, the metal salt may be dissolved in water or an aqueous medium containing a cosolvent such as propylene glycol, glycerol, or ethanol; salts, such as sodium chloride or other flavoring ingredients; pH buffers; chelating agents; glucose; gums; and/or preservatives.

The advantages of use of the pouch over direct dissolution of the system in the product to be treated are as follows:

1. The redox reactions between the metal, oxygen scavenger, and oxygen take place inside the pouch, so that no radicals are released into the food (in the case of $Fe^{3+}$), and the scavenger is not in direct contact with reducible dyes, such as anthocyanins and azo dyes. These compounds undergo a color change upon reduction by ascorbic acid.

2. The pouch can be added after the product has been heat-treated.

Figure 6:
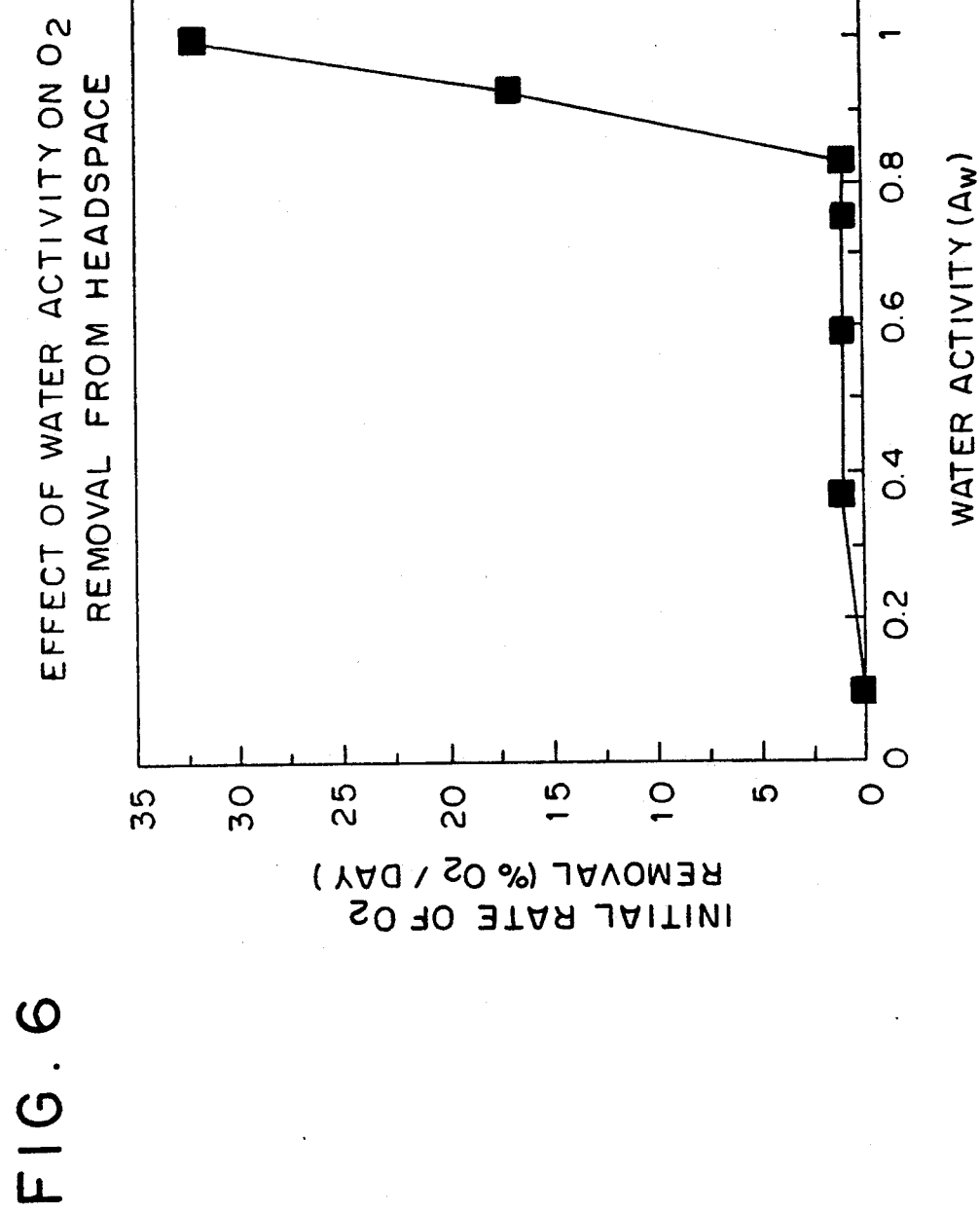
FIG. 6 shows the effect of water activity ($a_w$) on oxygen utilization by the system at 25° C. Solutions of variable water activity containing 40 ppm copper gluconate and 0.2% ascorbic acid in 50 mM Tris, pH 7.4, were stored in oxygen-impermeable plastic tubs for 28 days. Headspace oxygen was withdrawn with a hypodermic syringe and analyzed using an oxygen analyzer. Variable water activities were achieved by saturating the solutions with the following salts: LiCl (0.1), $MgCl_2$ (0.37), NaBr (0.59), NaCl (0.75), KCl (0.83), $K_2SO_4$ (0.93), no salt (1.00).

3. Use of a pouch is particularly useful for products having low water activity. The system removes $O_2$ at a slower rate when it is added directly to a food product having a water activity less than 0.8, (FIG. 6).

Figure 7:
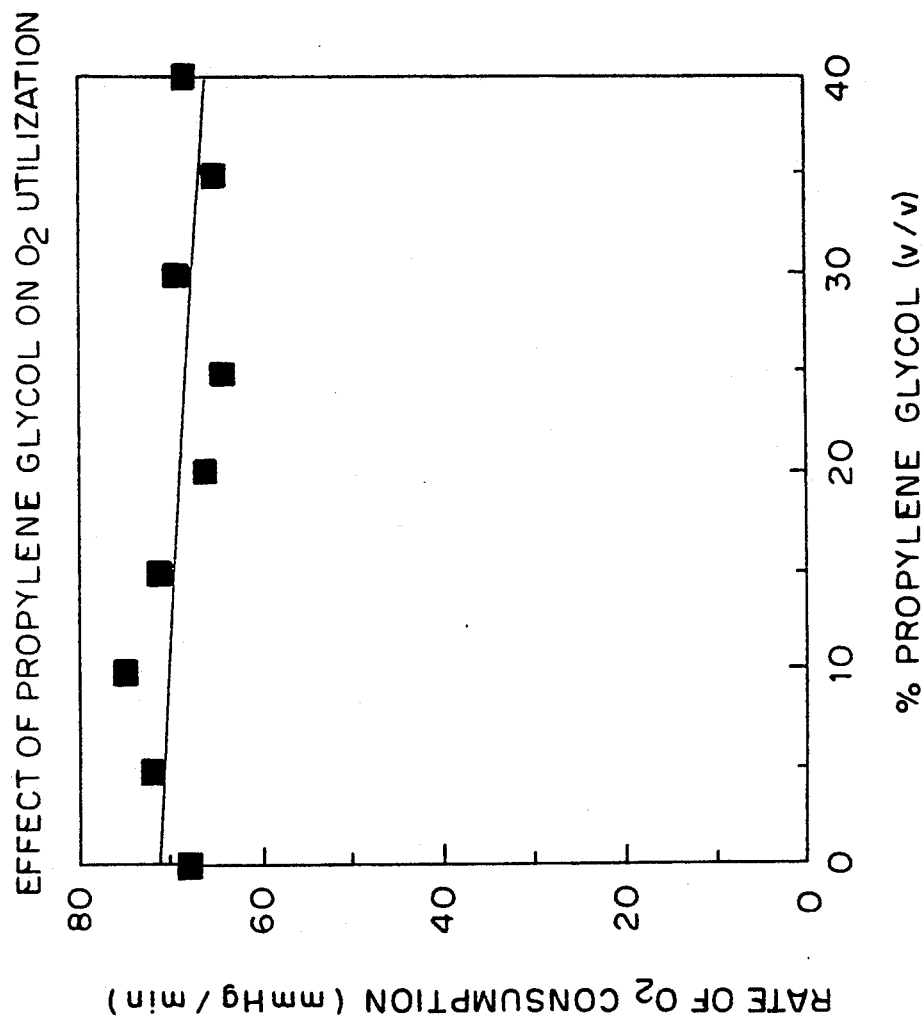
FIG. 7 shows the effect of propylene glycol on copper-mediated oxygen utilization. Initial rates were measured in 50 micromolar copper sulfate, 1 mM sodium ascorbate, and 50 mM Tris, pH 7.4, at 25° C.

4. The pouch can be used in packages where the product is subjected to freezing conditions, i.e., below 0° C. The Oxysorb system was found to be completely inactive in ice, so it may be ineffective in frozen foods that contain little bound water. In this case, wherein lipid peroxidation is often the predominant mode of product failure, the metal/ascorbate system is dissolved in 40% propylene glycol and added to the food in a pouch. The rate of oxygen removal was not affected significantly by the addition of this freezing point depressant (FIG. 7). Propylene glycol is used because of its low viscosity, lack of toxicity, and low cost, although other freezing point depressants can also be used. A corrugated surface may be provided for the package to increase the surface area thereof, accelerating diffusion of oxygen into the pouch.

A study was conducted to determine the rate of oxygen removal by pouches containing the system of the present invention as a function of temperature, and to compare this pouch method to the direct dissolution method.

A solution was prepared containing 13.7% ascorbic acid, 40 ppm copper gluconate, 50 mM Tris buffer at pH 7.4, and 25% propylene glycol to prevent freezing. The pouches were an average size of about 6×4 cm (48 $cm^2$) and contained about 22 ml of the solution. The polyethylene pouch film was a high water barrier and a low oxygen barrier. The pouches were filled and sealed to contain no headspace. Each pouch was then sealed inside a 6 oz. polypropylene tub with an aluminum foil lid. The samples were divided equally and stored at 100° F. (38° C.), 70° F. (21° C.), 40° F. (5° C.), or −10° F. (−24° C.). Headspace oxygen evaluations were done intermittently, depending upon the storage temperature and the predicted rates.

Figure 8:
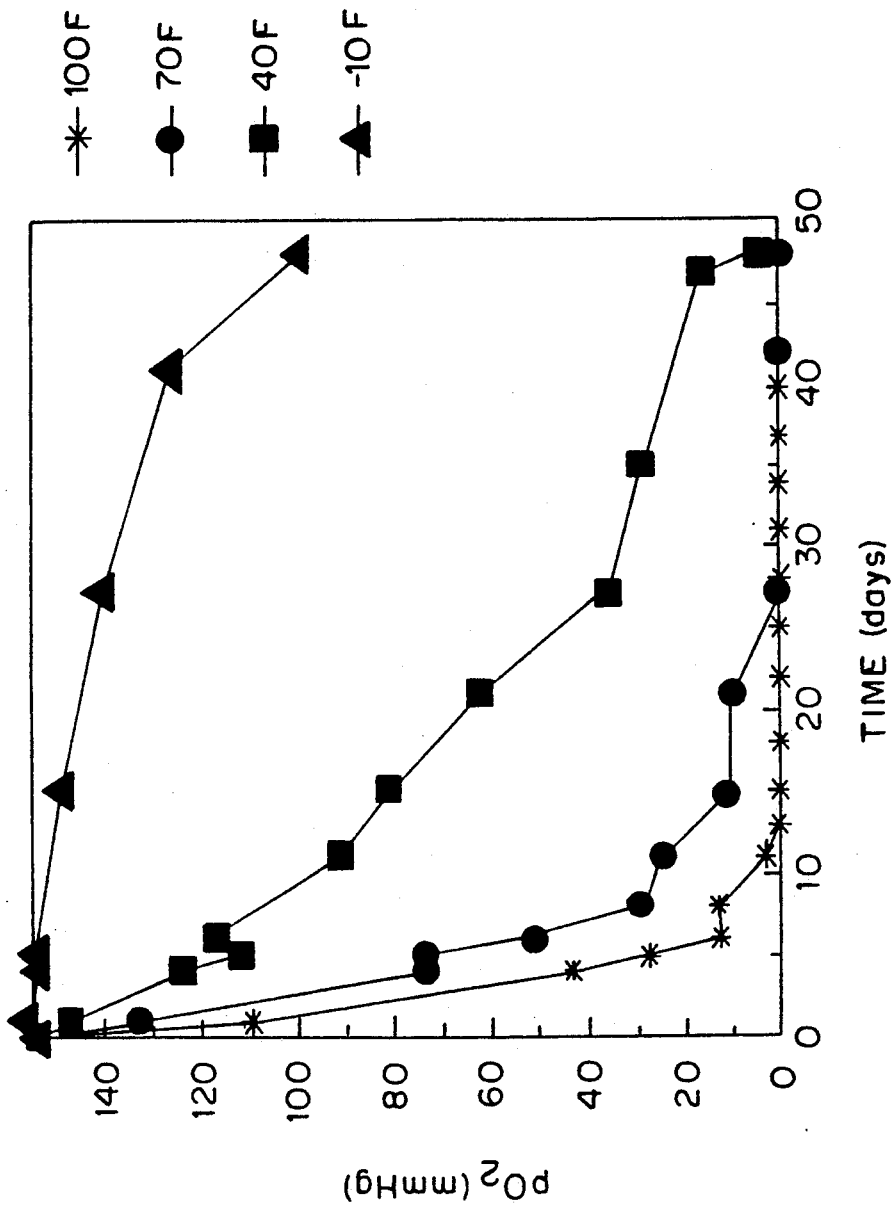
FIG. 8 shows the effect of temperature on the rate of oxygen diffusion into an Oxysorb pouch. A polyethylene pouch (48 cm$^2$) containing 22 ml of Oxysorb was sealed inside a 6 oz. oxygen-impermeable tub. Headspace $O_2$ was determined after various time intervals; each time point represents a different sample.

FIG. 8 illustrates the rates of oxygen depletion using the pouches at different temperatures. The rate of the reaction is faster the higher the temperature. The removal rate depends on temperature, pouch area, initial oxygen concentration, and it is independent of the headspace (i.e., a given pouch removes 10 ml at the same rate as 100 ml).

Figure 9:
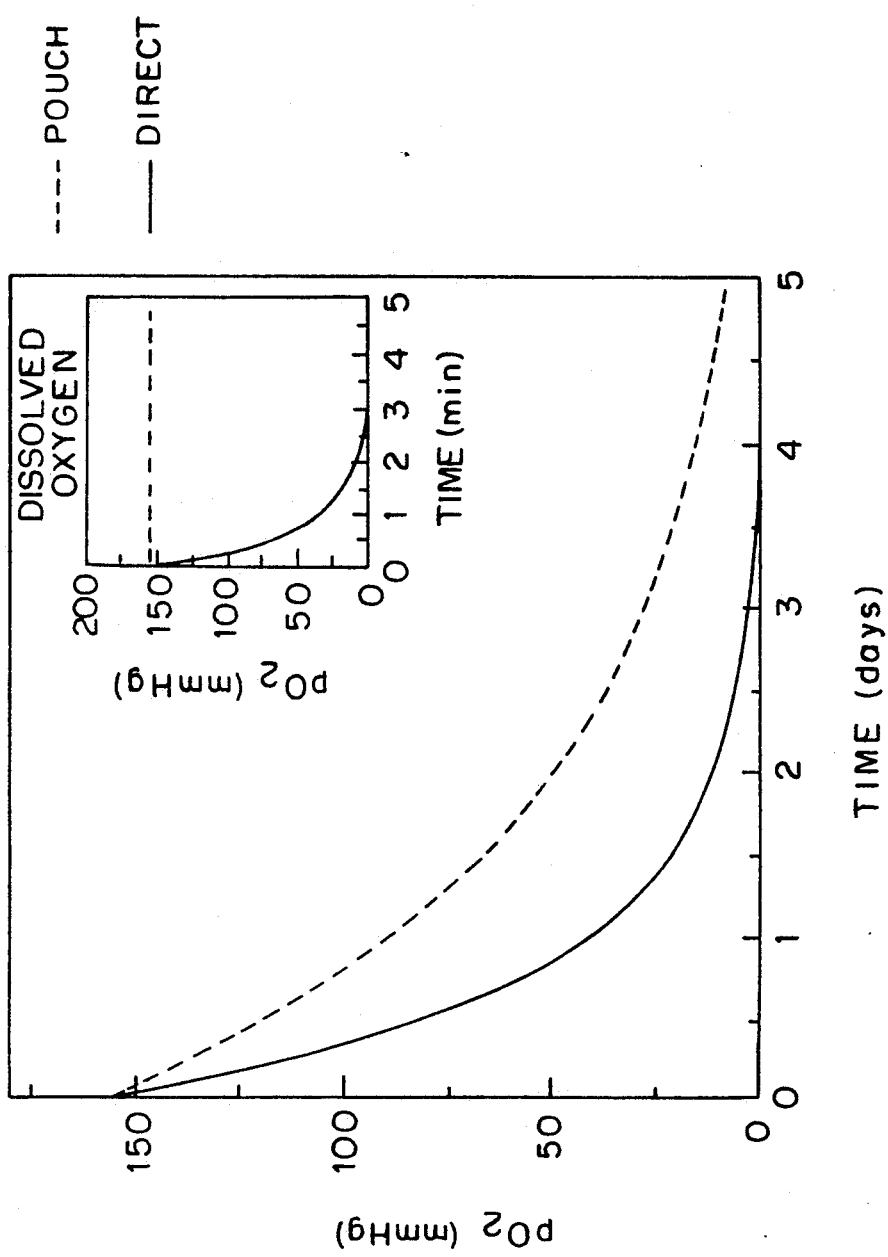
FIG. 9 shows the effect of the Oxysorb addition method (direct dissolution vs. pouch addition) on the rate of oxygen removal from solution and headspace.

Although the pouches were found to work in the tested range of temperatures, the rates of oxygen removed from the headspace are roughly half those of direct addition, as shown in FIG. 9. Furthermore, dissolved oxygen is removed within one minute by direct addition, while it is removed at the same rate as headspace oxygen (approximately 10 days) in the pouch method, cf. FIG. 9.

Figure 10:
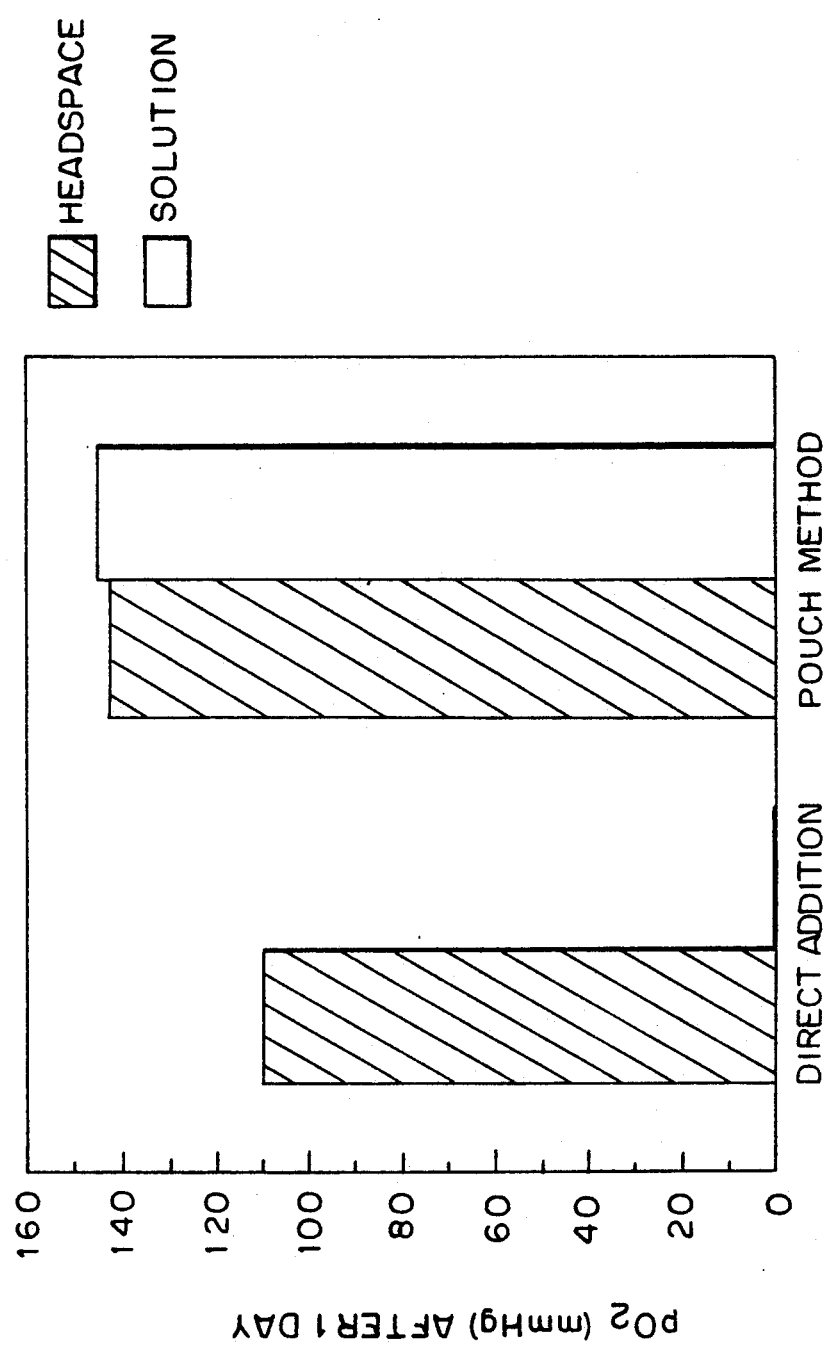
FIG. 10 shows the oxygen gradient between solution and headspace for the pouch method versus direct addition of Oxysorb.

This large difference arises from the opposite driving forces in the two experiments. In the direct addition method, the dissolved oxygen tension is zero after one minute. This sets up a large, steep oxygen gradient across the air-liquid interface which drives oxygen from the headspace into the solution, cf. FIG. 10. In the pouch method, however, the oxygen tension in solution and headspace remain virtually identical throughout shelf-life. Slow oxygen removal from the headspace by the pouch creates an infinitesimal gradient, which forces reequilibration between headspace and solution by slow movement of oxygen from solution to headspace, as shown in FIG. 10.

The addition of the system of the present invention also provides a foolproof and rapid method for detecting leaks and misformulated batches. Samples that contain both copper and ascorbic acid and that have been sealed properly develop a strong vacuum after 24 hours. The aluminum foil packaging is very tight and concave.

It has been noted that when the system of the present invention is added to a food system in a pouch, the package changes shape with different stages of the reaction. Within one day, a vacuum is created as the oxygen is depleted. As the reaction proceeds, the vacuum decreases. After about 20 to 28 days, a ballooning effect is evident. Apparently, the reaction produces carbon dioxide in excess of the depletion of oxygen. One of the indicators of this reaction is a color change of the system from a clear liquid initially to a dark brown.

Trials were conducted to determine the concentration of carbon dioxide produced and to ascertain if pH and ascorbic acid concentration influence the amount of carbon dioxide production.

Ten ml of a solution of 40 ppm copper gluconate and variable concentrations of ascorbic acid were sealed in a 6 oz. empty, oxygen-impermeable tub and stored in the dark at ambient temperature. The tubs were then analyzed for oxygen, carbon dioxide, and nitrogen on a gas chromatograph. The variables were:

pH 7.4 with 15% ascorbic acid, 10% ascorbic acid, 5% ascorbic acid, 0.2% ascorbic acid;

pH 3.0 with 15% ascorbic acid, 10% ascorbic acid, 5% ascorbic acid, and 0.2% ascorbic acid.

Figure 11:
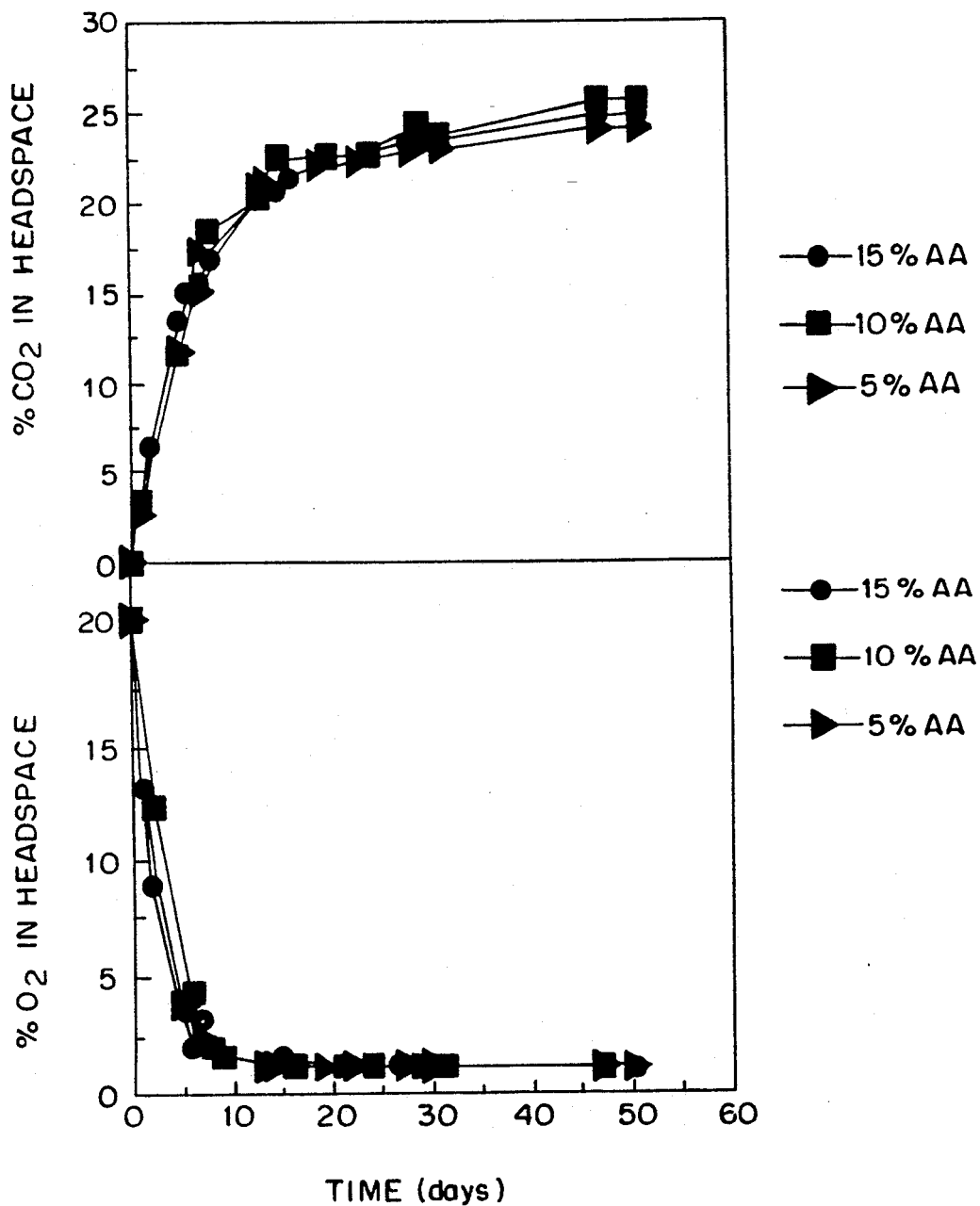
FIG. 11 shows the effect of ascorbic acid concentration on the rates of $CO_2$ generation and $O_2$ utilization at pH 7.4.
Figure 12:
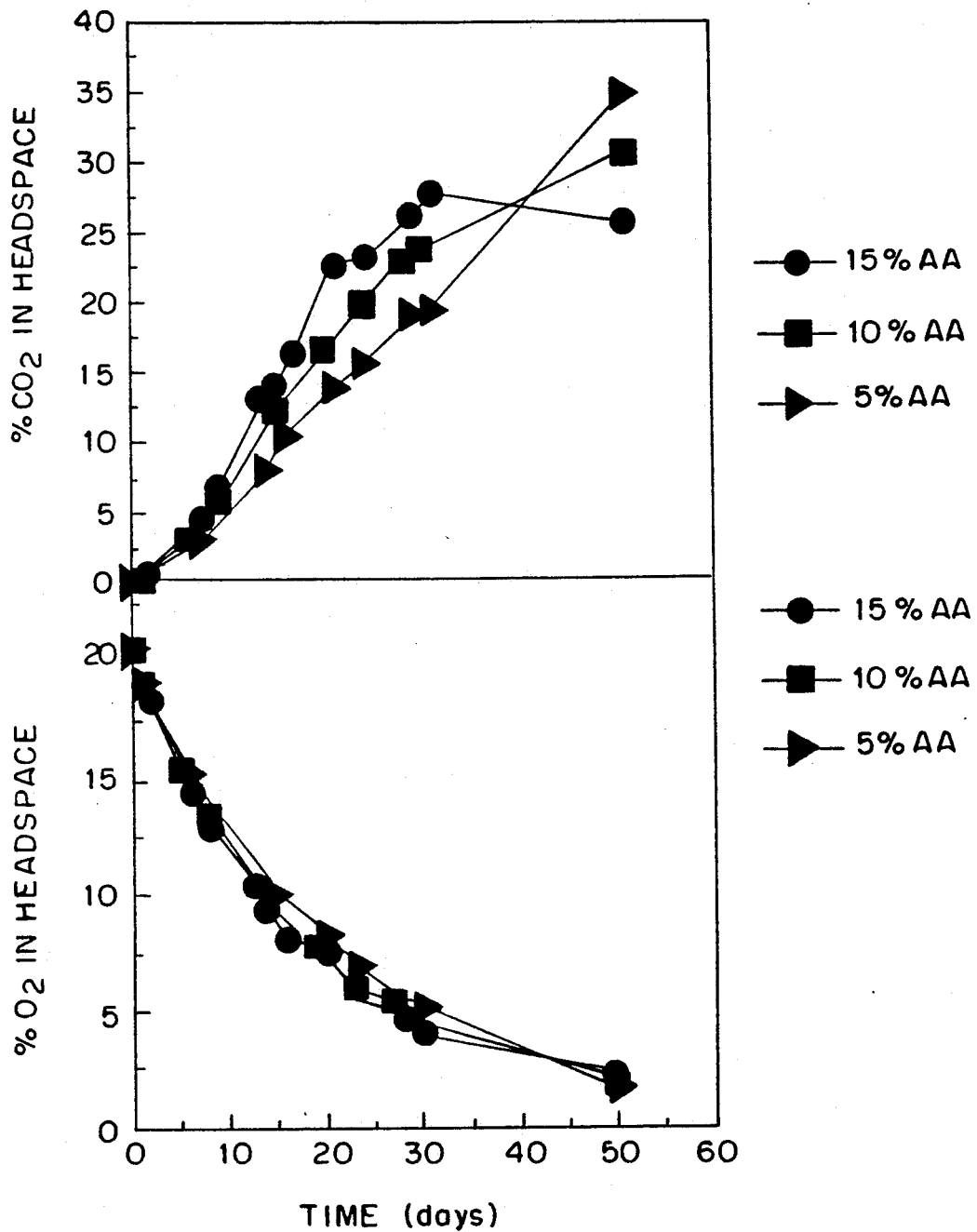
FIG. 12 shows the effect of ascorbic acid concentration on the rates of $CO_2$ generation and $O_2$ utilization at pH 3.0.

FIGS. 11 and 12 show that the concentration of ascorbic acid had no significant effect on the rate of oxygen utilization, the rate of decarboxylation, and the total amount of carbon dioxide produced. This indicates that diffusion of oxygen into the liquid is the rate-limiting step, and the quantity of carbon dioxide formed depends strictly on the amount of oxygen available, i.e., each molecule of ascorbic acid that has been oxidized by oxygen to dehydroascorbic acid undergoes a fast and subsequently a slow decarboxylation to form a product of unknown structure. The second decarboxylation is responsible for the large positive pressure inside food packages containing a pouch. Ballooning appears as soon as the combined amount of carbon dioxide and remaining oxygen exceed 21% of the headspace.

Development of positive pressure in food packages containing a pouch according to the present invention occurs primarily with foods of very low carbon dioxide solubility, such as solids. Flushing with nitrogen or decreasing the headspace to reduce the initial oxygen level are two approaches to minimizing this problem. However, in some cases, high levels of carbon dioxide may be beneficial, as they are toxic to many microorganisms.

A concern was raised over the amount of water generated by the system of the present invention, particularly in dry foods. However, it was found that 0.2% ascorbic acid in any food was calculated to produce only 0.018% moisture, while it depletes a substantial quantity of oxygen. One gram of a food containing 0.2% ascorbic acid has the capacity to remove all of the oxygen from 0.61 ml air. Therefore, the system of the present invention has no noticeable effect on the moisture of even very dry food, such as corn chips.

The blue color of the copper salts does not affect the visible color of the food at the very low concentrations used in the present invention. Both ascorbic acid and copper contribute no odor or flavor to the food. The pH remains unchanged in most food systems because of the food's buffering capacity.

With regard to current FDA regulations, copper may be added to foods and pharmaceuticals for oral ingestion in the form of copper gluconate as a dietary supplement not exceeding 50 ppm (equivalent to 7.0 ppm copper), or as a processing aid not exceeding good manufacturing practices. Ascorbic acid can be labelled as vitamin C or as ascorbic acid, depending upon the type of food or pharmaceutical product involved.

At a pH of 7.4, 90% of dissolved oxygen is removed by 100 micromoles of copper sulfate (6.4 ppm copper) and 2 mM sodium ascorbate (0.040%) within 1.8 minutes, as shown in FIG. 1. No oxygen utilization is observed in the presence of copper alone or ascorbate alone. The initial rate of oxygen removal in the presence of copper and ascorbate was calculated to be 133 mmHg/min. As discussed previously, the mechanism for oxygen removal by copper and ascorbate consists of a reduction of $Cu^{2+}$ to $Cu^+$ by ascorbate, followed by a reduction of oxygen by $Cu^+$ to regenerate $Cu^{2+}$.

Figure 13:
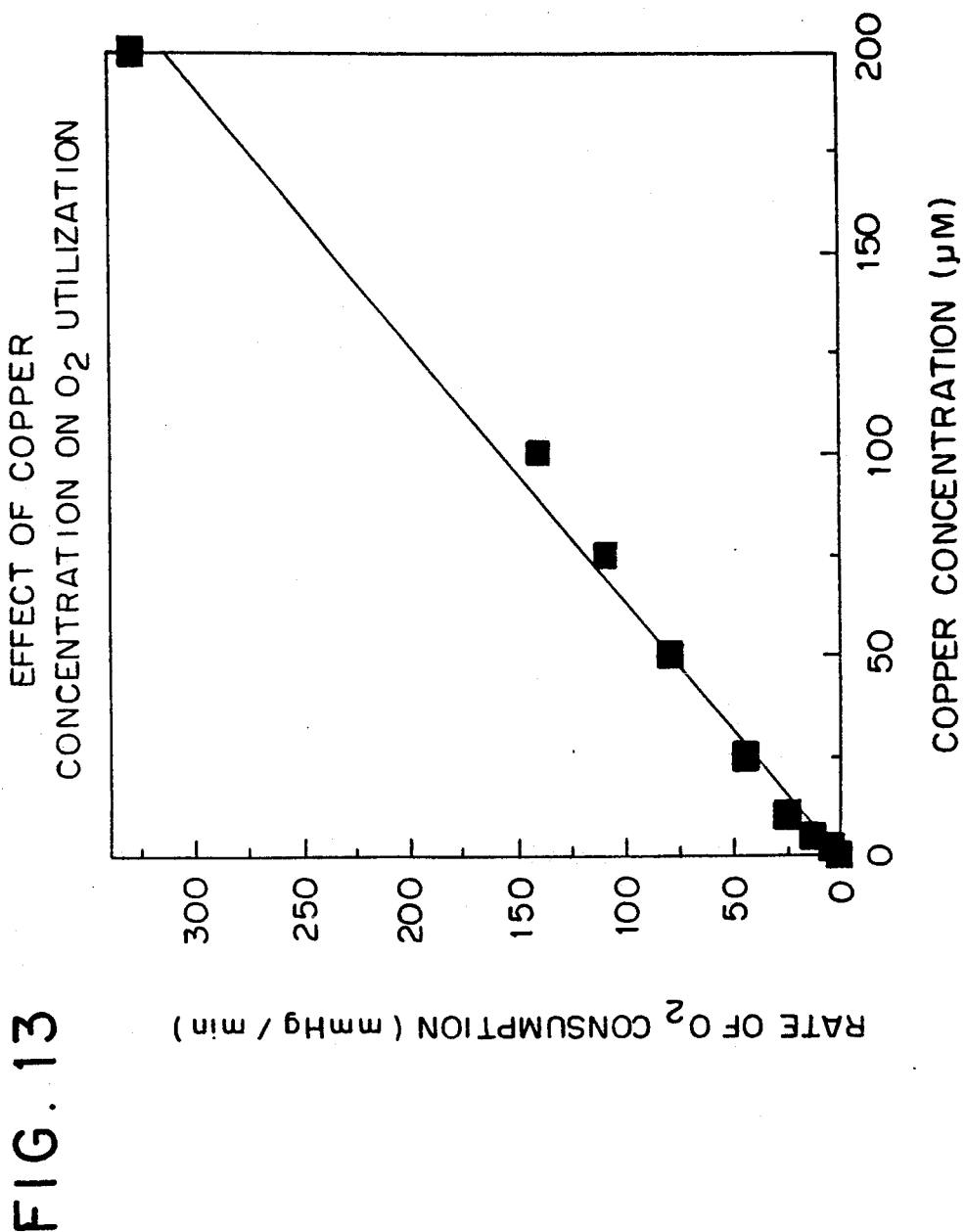
FIG. 13 shows the effect of copper concentration on oxygen utilization in 1 mM sodium ascorbate and 50 mM Tris, pH 7.4, at 25° C. Each point represents the initial slope of oxygen curves shown in FIG. 1 (initial rates). The solid line shows the best fit calculated from a linear regression analysis.

The rate of this reaction is linearly dependent upon the copper concentration, as shown in FIG. 13. Even 2 micromolar $Cu^{2+}$ catalyzes measurable oxygen consumption. The concentration of the copper in the system of the present invention can vary over a wide range, from about 1 ppm to about 70 ppm in the system being protected, the upper limit also being dependent upon FDA limitations in upper centrations on food. However, for optimum performance, a minimum of at least 3 ppm is recommended. At low pH, i.e., at pH less than 6, the concentration of the copper is preferably at least 6 ppm.

Figure 14:
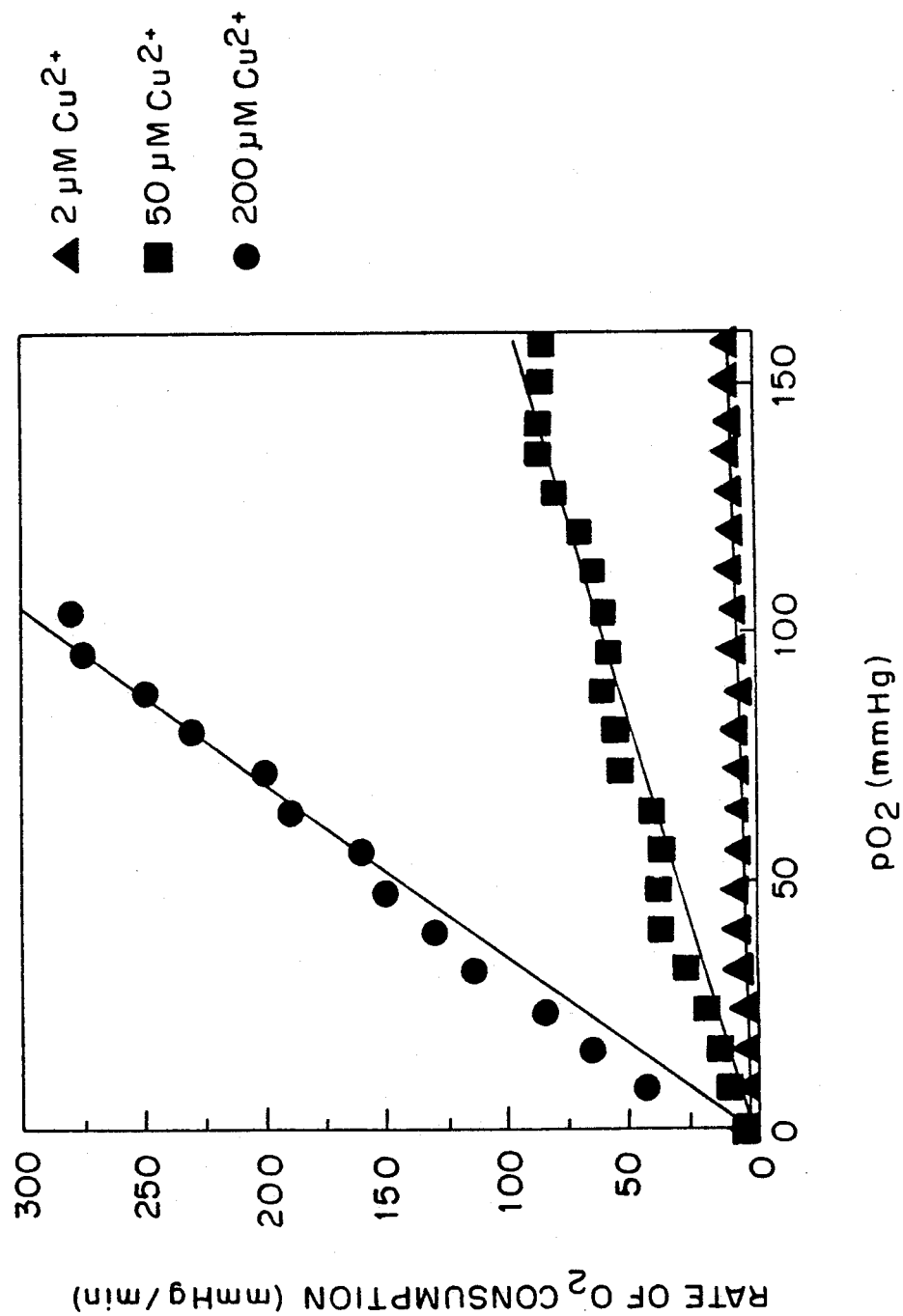
FIG. 14 shows the effect of oxygen tension on oxygen utilization at various concentrations of copper. The experiment were carried out at 25° C. in 1 mM sodium ascorbate, 50 mM Tris, pH 7.4, and increasing concentrations of copper sulfate.

The rate is also directly proportional to the oxygen tension over a wide range of copper concentrations, as shown in FIG. 14.

Figure 15:
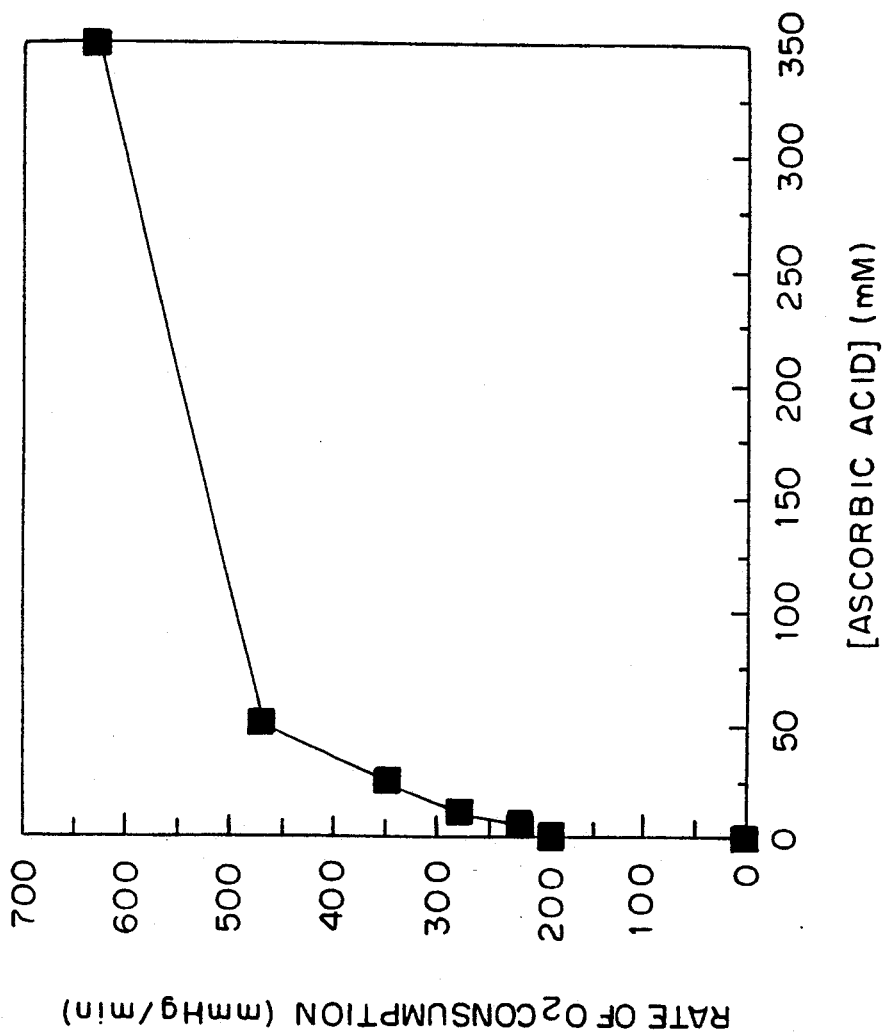
FIG. 15 shows the effect of ascorbate concentration on copper-mediated oxygen utilization. Each experiment was carried out at 25° C. in 50 micromolar copper sulfate, 50 mM Tris, pH 7.4, and increasing amounts of sodium ascorbate.

Ascorbic acid affects the rate of oxygen depletion primarily at low concentrations, as seen in FIG. 15. At high concentrations, the dependence is partly due to increasing transition metal contamination.

Figure 16:
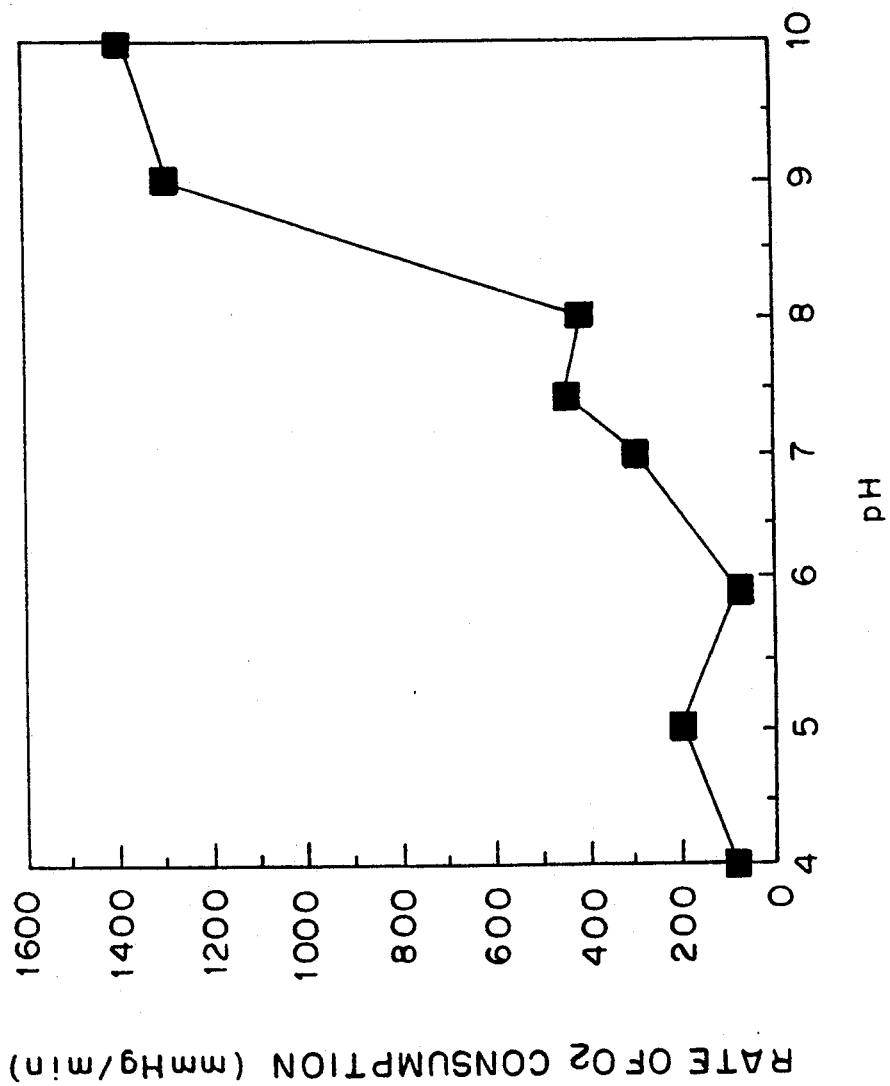
FIG. 16 shows the effect of pH on copper-mediated oxygen utilization in 100 micromolar copper sulfate and 2 mM sodium ascorbate at 25° C. The following buffers were used to achieve the desired pH values: acetic acid, pH 4.0; acetic acid, pH 5.0; imidazole, pH 6.0; imidazole, pH 7.0; Tris, pH 7.4; Tris, pH 8.0; glycine, pH 10.0.

As can be seen from FIG. 16, the rate of oxygen utilization increases with pH. The two exceptions at pH 6.0 and 8.0 may arise from copper-buffer interactions, since several of the pH buffers form weak chelates with copper.

Oxygen utilization is fairly temperature-dependent. From the Arrhenius plot shown in FIG. 17, a temperature coefficient ($Q_{10}$) of 2.0 was calculated, which means that at a freezer temperature of $-12°$ C. the rate will be 6% of that at 25° C.

The Oxysorb system of the present invention is also effective in the presence of chelating agents, such as citric acid, EDTA, phosphate compounds, L-histidine, glycine, and mixtures thereof. The chelating agents used for this experiment were glycine, L-histidine, phytic acid, and EDTA. Purified water and Tris were dispensed into the vial, and then 1 mM chelating agent and 100 $\mu$M copper gluconate were added. Upon stabilizatioh the oxygen electrode, the ascorbic acid was introduced and the reaction quickly took place. As illustrated in FIG. 18, in the case of glycine, the initial rate was faster than that of the control, which contained no chelating agent. Phytic acid was slightly slower than the control. Histidine caused some inhibition. EDTA almost completely inhibited the reaction.

Another experiment was designed to substitute a variety of transition metals and reducing agents in place of copper and ascorbate. The transition metals were ferric chloride, manganese sulfate, cobalt chloride, and chromium chloride. The final concentration of these metals was 100 micromolar in 10 mM ascorbic acid and 50 mM Tris buffer, pH 7.4. To start the reaction, the metal was added to these solution, and the removal of dissolved oxygen was monitored using a Clark electrode.

Referring to FIG. 19, it is evident that the copper gluconate control is the best catalyst for this reaction. However, the other metals do demonstrate the ability to promote the oxygen removal reaction, although the initial rates are significantly slower.

The reducing agents substituted for ascorbic acid were sodium sulfite, cysteine, and catechol. The order of addition was purified water, Tris, and 1 mM reducing agent. When the electrode stabilized, the copper gluconate was added. FIG. 20 illustrates that the ascorbic acid control is the most efficient reducing agent compared to the substitutes. Nevertheless, the alternatives were somewhat effective, cysteine being more reactive than sulfite and sulfite being more reactive than catechol.

The system of the present invention was evaluated to determine the effectiveness of the system in various water activity systems.

Six salt solutions were prepared to provide a range of water activities between 0.1 and 1.0. The system of the present invention was added, and the solutions were sealed in oxygen-impermable containers. The headspace of these containers was analyzed for % oxygen over a period of 28 days.

From the results shown in FIG. 6, the system of the present invention was significantly faster at high water activities. In systems with a water activity lower than 0.8, it may be advisable to add the system encased in a pouch. A benefit of this great dependence on water activity is the stability of the Oxysorb system in a dry system. Thus, copper and the oxygen scavenger may be incorporated into a dry preblend and stored for several months before being added to the remaining food components.

Experiments were conducted to determine the effect of protein on the reaction of the Oxysorb system. Using a Clark electrode, the oxygen consumption was measured in solutions containing 50 mM Tris, pH 7.4, 0.2% ascorbic acid, 40 ppm copper gluconate, variable amounts of ovalbumin, with and without 2 mM glycine. The order of addition was water, Tris, glycine, copper gluconate, ovalbumin, and ascorbic acid.

FIG. 21 shows that ovalbumin binds copper with a high affinity and thereby greatly decreases the rate of oxygen removal. The addition of glycine, a chelating agent, diminished this protein effect by competing for copper and making it available for reduction by ascorbic acid. Despite the great inhibitory effect of protein, the system of the present invention still effects complete oxygen removal within 25 minutes at 25° C. However, it may be desirable to add a chelating agent, such as glycine, to certain types of foods that already have depressed Oxysorb activity due to low $a_w$/temperature or high viscosity.

A number of oil-based food systems undergo oxidative rancidity and develop off-flavors, so that a system to scavenge oxygen from such systems would aid in preserving such foods. For such a system, a fat-soluble derivative of the ascorbic acid/copper combination was used. Oxidative damage was measured by peroxide value (PV) and the thiobarbituric acid (TBA) test for malondialdehyde (MDA).

The fat-soluble system of the present invention comprises ascorbyl-6-palmitate in absolute ethanol and copper caprylate in ethanol. The final concentrations were 0.47% ascorbyl palmitate and 30.8 ppm copper caprylate in the emulsions.

Four different emulsions and oils were used: water-in-oil (w/o), oil-in-water (o/w), liquid shortening, and solid shortening. None of the oils contained antioxidants such as BHA. Xanthan gum (1%) and sodium stearoyl lactylate (0.5%) were added to the o/w to thicken and emulsify, respectively. Mono-diglycerides were added to the w/o emulsion to stabilize it. The two oils did not contain any emulsifiers.

The emulsions were prepared and dispensed into polypropylene tubs and small 60 ml oxygen-impermeable plastic jars with no headspace. The emulsions were stored at ambient temperature and evaluated intermittently. The tubs were used for headspace oxygen analysis, and the jars were evaluated for PV and MDA.

The MDA values of all emulsions and oils containing the Oxysorb system never exceeded 0.5, whereas the controls increased to 2.8 mg of MDA/1, as shown in FIGS. 22 and 23. Similarly, the peroxide value of all emulsions and oils was substantially reduced by the addition of Oxysorb, shown in FIGS. 24 and 25. These studies demonstrate that copper-ascorbate stabilizes both aqueous and oil systems and protects them against oxidative damage and food spoilage.

It has also been found that the system of the present invention strongly inhibits the activity of polyphenol oxidase (tyrosinase), the enzyme primarily responsible for the browning of vegetables and fruits. Bruising, cutting, and processing this type of food accelerates enzymatic browning by releasing both enzyme and substrates and bringing them into close vicinity. Since oxygen is absolutely essential for these reactions to occur, the copper-ascorbate system was shown to substantially retard the browning of cut potatoes and of guacamole.

In the following experiment, pure mushroom tyrosinase (polyphenol oxidase) and the substrate DL-dihydroxyphenylalanine (DOPA) were used to demonstrate the inhibition of browning by the Oxysorb system of the present invention.

Five hundred microliters of deionized water, 200 microliters of 2% ascorbic acid, and 200 microliters of 400 ppm copper gluconate were added to 1000 microliters of 0.6 mg/ml DOPA in 200 mM phosphate, pH 6.5. The mixture was allowed to stand for ten minutes to ensure that all of the oxygen had been removed. Then 100 microliters of 0.4 mg/ml of polyphenol oxidase was added, and the absorption was measured spectrophotometrically at 475 nm at 30° C. for one hour (read versus the complete reaction mixture but without the enzyme). The enzyme is completely inhibited by the system of the present invention. The control reaches an absorbance of 0.36 after 30 minutes, as shown in FIG. 26.

The system of the present invention has also been shown to inhibit the growth of a number of microorganisms that are undesirable in food, pharmaceutical, and cosmetic products. To determine the antimicrobial effects of Oxysorb, 10 ml of broth in 16×100 screw-capped tubes were inoculated with diluted, overnight cultures to achieve an initial population of 100 to 1000 cells/ml. Nutrient broth was used for *E. coli* and *Pseudomonas fluorescens*; fluid thioglycollate medium was used for *Clostridium sporogenes*. Following inoculation, sodium ascorbate was added at a level of 0.2%, then 88 μM metal salt (copper gluconate, cobalt chloride, or ferric chloride). Ascorbate, copper, cobalt, and iron solutions were prepared and filter sterlized just prior to use. Tubes were incubated at 25° C. with caps tightened, unless they were placed in anaerobic (Gas Pak) jars. Anaerobically incubated tubes had loose caps to allow for generation of an anaerobic environment in the tube headspace. Samples from two individual tubes were plated periodically.

It was found that ascorbate alone had little effect on the growth of *E. coli*, as shown in Table I. Anaerobic incubation with and without ascorbate slightly reduced the maximum population, although the growth rate was not affected. Copper alone reduced both the growth rate and the maximum population for *E. coli* in nutrient broth (Table I). Anaerobic incubation with copper alone further suppressed growth.

The system of the present invention, containing both copper and ascorbate, greatly inhibited the growth rate of $E.$ $coli$ in sealed tubes, and completely inhibited the growth of the organism for four days when the tubes were incubated in an anaerobic jar, as shown in FIG. 27.

Cobalt and cobalt/ascorbate affected $E.$ $coli$ growth in a manner similar to copper and copper/ascorbate, as shown in Table I. Growth was slowed but not stopped. Iron and iron/ascorbate, however, had no effect on the growth of $E.$ $coli.$ $Pseudonomas$ $fluorescens$, an obligate aerobe, responded in a manner similar to $E.$ $coli$ (cf. Table II), i.e., growth in the presence of iron or iron/ascorbate did not differ from the control. Cobalt, cobalt/ascorbate, and copper/ascorbate (Oxysorb) slowed the growth of the organism. Oxysorb also markedly inhibited yeast growth over a 4-day period (FIG. 28), whereas copper alone showed no toxicity under the same conditions. Similarly, the system has been found to suppress the growth of Salmonella and Staphylococcus aureus, two other food spoilage pathogens. Conversely, Clostridium sporogenes, an obligate anaerobe, and lactic acid bacteria, were not inhibited by any of the treatments.

TABLE I

Growth of $E.$ $coli$ in nutrient broth with and without sodium ascorbate (0.2%) and metals (88 μM sodium).

| Time (days) | 0 | 0.25 | 1 | 2 | 5 |
|---|---|---|---|---|---|
| Control | 180 | 1800 | $2.1 \times 10^8$ | $5.5 \times 10^8$ | $2.5 \times 10^8$ |
| Ascorbate | 350 | 4600 | $1.6 \times 10^8$ | $4.6 \times 10^8$ | $3.8 \times 10^8$ |
| $Fe^{3+}$ | 420 | 6400 | $2.1 \times 10^8$ | $3.4 \times 10^8$ | $1.5 \times 10^8$ |
| $Fe^{3+}$ & Asc. | 100 | 11000 | $6.5 \times 10^8$ | $5.3 \times 10^8$ | $2.7 \times 10^8$ |
| $Co^{2+}$ | 430 | 690 | $8.1 \times 10^5$ | $2.2 \times 10^6$ | $4.5 \times 10^8$ |
| $Co^{2+}$ & Asc. | 430 | 780 | $8.8 \times 10^5$ | $2.2 \times 10^8$ | $6.6 \times 10^8$ |
| $Cu^{2+}$ | 510 | 3100 | $4.7 \times 10^7$ | $4.8 \times 10^7$ | $7.3 \times 10^6$ |
| $Cu^{2+}$ & Asc. (Oxysorb) | 700 | 440 | $1.1 \times 10^5$ | $2.3 \times 10^6$ | $5.5 \times 10^7$ |

TABLE II

Growth of $Pseudomonas$ $fluorescens$ in nutrient broth with and without sodium ascorbate (0.2%) and metals (88 μM).

| Time (days) | 0 | 0.25 | 1 | 4 | 6 |
|---|---|---|---|---|---|
| Control | 150 | 210 | $8.1 \times 10^7$ | $1.4 \times 10^8$ | $7.1 \times 10^8$ |
| Ascorbate | 160 | 170 | $4.7 \times 10^7$ | $7.2 \times 10^8$ | $2.7 \times 10^8$ |
| $Fe^{3+}$ | 130 | 160 | $6.2 \times 10^7$ | $8.1 \times 10^7$ | $5.1 \times 10^7$ |
| $Fe^{3+}$ & Asc. | 150 | 280 | $2.8 \times 10^7$ | $3.3 \times 10^7$ | $1.1 \times 10^8$ |
| $Co^{2+}$ | 150 | 65 | $1.9 \times 10^6$ | $5.6 \times 10^8$ | $5.5 \times 10^7$ |
| $Co^{2+}$ & Asc. | 170 | 170 | $6.4 \times 10^4$ | $2.0 \times 10^8$ | $1.7 \times 10^8$ |
| $Cu^{2+}$ | 140 | 180 | $9.6 \times 10^7$ | — | $1.6 \times 10^8$ |
| $Cu^{2+}$ & Asc. (Oxysorb) | 140 | 29 | $1.1 \times 10^5$ | $7.6 \times 10^6$ | $1.8 \times 10^7$ |

The system of the present invention slowed the growth of facultatively aerobic microorganisms studied by an unidentified mechanism, but had no effect on aerotolerant lactic acid bacteria or anaerobic bacteria. Oxygen deprivation did not appear to be the mode of action in that growth of the strict anaerobic $P.$ $fluorescens$ was similar to that of facultative $E.$ $coli$. Also, the growth of $E.$ $coli$ in the presence of the system of the present invention was slower than that observed in the anaerobic environment of a Gas Pak jar. Furthermore, anaerobic incubation of $E.$ $coli$ in the presence of the Oxysorb system inhibited growth completely. The mechanism of inhibition is not yet known, however, it is likely to involve $H_2O_2$ (generated by $Cu^{2+}$ from $O_2$ and ascorbic acid) and hypochlorous acid (HOCl) (generated by $Cu^{2+}$ from $H_2O_2$ and chloride).

Ten kilograms of a mild salsa, pH 3.9, were produced and heated to 80° C., and then cooled to 24° C. To this was added 0.2% sodium ascorbate (10.1 mM) and 0.0040% (40 ppm) food grade copper gluconate (equivalent to 5.6 ppm copper = 88 micromolar). This was mixed, and 176 grams were placed into cylindrical 7.9-cm diameter plastic tubs with 48 ml headspace. An aluminum foil cover was heat sealed onto the tubs. The samples were stored under refrigeration for three months.

In the Mexican style salsa tested with the Oxysorb system, dissolved oxygen was rapidly depleted with a concentration of 5.6 ppm copper and 0.2% sodium ascorbate. However, as seen in FIG. 29, the consumption of oxygen from the headspace is diffusion-limited. The rate constant for the disappearance of oxygen is 0.12/day, calculated from a linearized semilog plot; this rate constant was used for the computer-generated rate, shown as a solid line. The low rate of diffusion presumably arises from the high viscosity of the salsa. Nevertheless, it has been found that the system of the present invention fully protects against discoloration, off-flavors, mushiness, syneresis, and microbial growth for more than 400 days, whereas the control reached the end of its shelf-life after 27 days.

Whenever possible, it is advantageous to accelerate oxygen diffusion by the following methods:
1. raising the initial storage temperature;
2. increasing the product surface;
3. agitating the product during the initial storage.

Additionally, in the case of very low diffusion rates and large head spaces, as in Mexican style salsas (176 ml salsa, 48 ml headspace in the standard package), partial flushing with nitrogen rationally may be used to maximize the efficiency of the system of the present invention.

The slow utilization of oxygen from the headspace of the control sample represents the oxidation of the product, leading to a number of undesirable sensory attributes. The rate constant for this slow oxygen utilization was calculated to be 0.011/day, assuming first order kinetics as in the case where the oxygen-absorbing system is used.

The above pilot plant experiment was repeated on a plant scale. It was found that the rate of oxygen removal from the headspace was about 30% greater than in the pilot plant, presumably because of agitation during shipment of the product, and an increased level of ascorbate (2% ascorbic acid rather than 0.2% sodium ascorbate). The rate of oxygen removal was slightly greater when Oxysorb was added to the cooled salsa than when it was added with the spice preblend and heat processed. However, after 420 days of refrigerated storage there was still no difference in sensory attributes between the two variables, and both products looked, smelled, and tasted significantly better than the nitrogen-flushed control. It should be noted that none of the products treated with the oxygen absorber of the present invention were flushed. No yeast, mold, or bacterial growth occurred in the samples containing the oxygen absorbing system of the present invention, even without any preservatives or a modified atmosphere.

It has been observed that the sauces used on frozen and refrigerated pizzas often oxidize during shelf-life, which causes color and flavor changes. The sauce may become unacceptably orange and/or lose its tomato flavor. Experiments were conducted to determine the efficacy of the Oxysorb system of the present invention in stabilizing pizza-type sauces.

The formulas for the control and the Oxysorb system containing sauces were as follows:

|  | Weight (grams) |
| --- | --- |
| Control |  |
| Tomato paste | 1559 |
| Water | 2914 |
| Soybean oil | 150 |
| Spice blend | 360 |
| Oxygen Scavenging System |  |
| Tomato paste | 1559 |
| Water | 2905 |
| Soybean oil | 150 |
| Spice blend | 340 |
| Ascorbic acid | 20 |
| 2.2% Aqueous copper gluconate solution | 9 |

The water and oil were weighed into a beaker and mixed in a mixer. Tomato paste was added by spoonfuls, after which the preweighed spice blend was added all at once. The sauce was mixed for 15 minutes at 1500 rpm. The ascorbic acid for the test samples was added to the spice blend. The copper gluconate was dissolved in water and added immediately before the sauce was packaged.

The product was packaged in 12 oz. oxygen impermeable plastic tubs with and without shredded cheese and sealed with foil lids. The samples were stored at −12° C. and evaluated for headspace oxygen, color, and flavor once per month.

The control product had color and flavor changes after one month and was unacceptable after three months of storage. The products containing the system of the present invention had not changed after four months of shelf-life even though headspace oxygen was removed by the Oxysorb system at a very slow rate, as shown in FIG. 30. The Oxysorb system also provided full protection against oxidative damage in the presence of cheese, an ingredient that normally greatly reduces shelf-life of pizza sauces by elevating the pH.

Guacamole is not shelf-stable primarily due to the instability of the color of the avocado when exposed to oxygen. The failure modes of currently available guacamole arise from four different reactions:

1. Polyphenol oxidase catalyzes enzymatic browning within a few hours of product preparation. This reaction is completely dependent on the availability of oxygen. The system of the present invention removes all dissolved oxygen within two minutes, and was found to completely inhibit the discoloration of guacamole for at least 80 days.

2. The high content of unsaturated lipids in avocados accelerates the onset of rancidity. By removing oxygen, the system stops the generation of off-flavors.

3. After about two months of shelf-life, oxidative damage to guacamole also manifests itself in the form of syneresis. This phenomenon arises from the oxidation of tomato particulates which causes cell wall injury and release of water. As above, by removing oxygen, the system of the present invention maintains textural integrity.

4. Growth of microorganisms gives rise to large gas pockets in guacamole, ballooning of the tub, and off-flavors. The system of the present invention strongly inhibits bacterial, yeast and mold growth, maintains a uniform product texture, and achieves a visible vacuum in the packaging tub due to removal of all headspace oxygen.

The guacamole was formulated as follows:

TABLE III

FORMULATION OF GUACAMOLE

| INGREDIENT | % CONTROL | % OXYGEN SCAVENGER |
| --- | --- | --- |
| Red Onions | 4.92 | 4.92 |
| Tomatoes | 21.88 | 21.88 |
| Avocadoes | 63.20 | 62.70 |
| Garlic Cloves | 0.25 | 0.25 |
| Olive Oil | 2.12 | 2.12 |
| Lemon Juice | 7.63 | 7.63 |
| Ascorbic Acid | 0 | 0.50 |
| Copper Gluconate | 0 | 0.004 |

$A_w = 0.92$
$pH = 4.1$

Each sample (160 ml) was weighed into 6-oz. oxygen-impermeable tub and a foil lid was hot sealed in place. The resulting headspace was approximately 50 ml. All samples were then stored in the refrigerator.

The produce was evaluated after 80 days, with the following results:

TABLE IV

GUACAMOLE EVALUATION AFTER 80 DAYS

|  | CONTROL | OXYGEN SCAVENGER |
| --- | --- | --- |
| Color | Dark green/brown | light green |
| Odor | Sour, awful | fresh |
| Flavor | not determined | fresh |
| % Headspace O$_2$ | 1.5* | 1.3 |
| Pressure in tub | Ballooning | Vacuum |
| Texture | Large gas pockets | Uniform |
| Visible mold growth | + | — |
| Total plate count/g | 480,000 | 6,000 |
| Overall acceptability | No | Yes |

*The low headspace oxygen of the control indicates that extensive oxidative damage to the prouct has occurred.

Another experiment was designed to demonstrate visually that the system of the present invention does inhibit polyphenol oxidase activity in potatoes. When potatoes are pureed and exposed to oxygen, they rapidly turn a reddish-brown within a few minutes and finally a black color after 7 days. When subjected to a chemical agent such as sodium bisulfite, this browning does not occur. This color change can also be prevented by the system of the present invention. A control of water and potato was pureed in a blender and placed into a screw top jar, filled to overflowing to minimize headspace. The same was done to a sample of potato and 40 ppm copper gluconate and 0.1% ascorbic acid in water. The jars were refrigerated and inverted frequently to disperse any foam formed.

The control started browning immediately upon processing. Browning due to the release of the polyphenol oxidase continued to increase until the solution became nearly black over a period of seven days. The potatoes exposed to the system of the present invention remained an off-white color, but the surface foam darkened slightly. When the samples were inverted to distribute the foam, the browning disappeared. This difference in the browning was also quantitated spectrophotometrically by measuring the absorption at 475 nm, as shown in FIG. 31.

Another experiment was conducted to determine if the system of the present invention could delay or prevent textural degradation of potatoes stored in water.

Raw potatoes were peeled, cubed, and immersed in water and in solutions of 40 ppm copper gluconate and 0.1% or 0.5% ascorbic acid. The samples were kept in uncovered glass mason jars at room temperature.

After one day, the control was a little cloudy, indicating microbes were growing. By day 2 the control had foam on top of the water surface, and the water was cloudy and turbid. Meanwhile, the other samples were clear and without foam. By day 3, the control smelled putrid and the potatoes were floating on top. The texture of the potatoes was gooey and sticky, and they had lost the cubed shape as they melted together. They exhibited a moldy color, and the water was yellowish and turbid. The 0.1% ascorbate sample was beginning to show slight turbidity and there were some bubbles on top, although there was no odor. The 0.5% solution had clear water, but some bubbles on top. On day 4, the 0.1% solution had some cubes floating, and murky water, while the 0.5% solution was still clear. After 7 days, the 0.5% solution had some turbidity, and some bubbles on top. After two weeks, the water was dark yellow, but none of the potatoes were floating, and they retained their shape and texture. After 16 days, some potatoes were floating and getting gooey. Sodium bisulfite, an inhibitor of enzymatic browning, had no effect at all on these chemical and microbiological events.

TABLE V

MICROBIOLOGICAL EVALUATION OF POTATO WATER

| | Total Plate Count* | Coliforms* | Anaerobes* |
|---|---|---|---|
| control | $2.8 \times 10^8$ | >2400 | $3.1 \times 10^7$ |
| 0.1% AA + 40 ppm $Cu^{2+}$ | $1.7 \times 10^8$ | >2400 | $3.2 \times 10^7$ |
| 0.5% AA + 40 ppm $Cu^{2+}$ | $2.5 \times 10^7$ | 93 | $1.5 \times 10^7$ |

*(microorganisms/ml)

Aseptically packaged corn in a microwaveable plastic container exhibits excellent microbiological stability when stored at 22° C., but it turns grey over 90 days. This greying phenomenon has been demonstrated to be a direct result of oxidative damage, presumably by oxygen dissolved in the water and present in the headspace.

The system of the present invention has been found to remove all of the dissolved oxygen within three minutes and the headspace oxygen within two to three days, because of the slow diffusion of oxygen into the water. However, during these initial two to three days, the actual concentration of oxygen in the water will be close to zero. Furthermore, the system will remove any oxygen permeating through the packaging material during storage. Therefore, the addition of the system should protect the corn from greying and extend its ambient shelf-life to at least two years. This technology is also applicable to the preservation of canned peas, asparagus, and other vegetables.

One problem associated with ready-to-spread frosting that limits its shelf-life is mold. To prevent mold growth, current products now use BHA, sorbate, and citric acid. The citric acid keeps the pH low and makes the sorbate effective. Other problems associated with these frostings are off-flavor development and color changes.

The system of the present invention was tested in ready-to-spread frostings packed in substantially oxygen-impermeable plastic tubs. After three weeks, these were pulled, and a microbial analysis was conducted. The results in Table VI indicate that the system of the present invention inhibits yeast growth when added directly to tho food product, and decreased rancidity of the product, as indicated by peroxide values (PV) and malondialdehyde (MDA) results:

TABLE VI

| | EVALUATION OF FROSTING | | |
|---|---|---|---|
| Sample | Yeast/gram | MDA (mg/kg) | PV (mg/kg) |
| control | 660000 | 0.21 | 3.1 |
| Oxysorb pouch | 95000 | | |
| Oxysorb dissolved directly in RTS | <100 | 0.15 | 0.4 |

The Oxysorb system is added in an amount effective to prevent objectionable and deleterious amounts of oxygen degradation and/or microbial growth. The measurements of both end results are known in the art e.g., organoleptically and plate counts, respectively.

The amounts of each system component and the system will depend on several factors. These factors include such things as: headspace amount, oxygen in the headspace, product to be protected, dissolved and contained oxygen, packaging permeability, shelf-life, storage temperature, etc. Government regulations and taste of the system can also limit the amounts. Thus, the amounts needed can vary widely but can be easily determined.

For food products, copper in the range of between about 1 ppm and about 7 ppm and ascorbate in amounts in the range of between about 0.05% and about 1% have been found effective for use in relatively high oxygen impermeable packaging.

The foregoing description of the specific embodiment will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. In a packaged ingestible product comprising a substantially non-oxygen permeable package and, contained therein, an ingestible product and an oxygen scavenging composition, the improvement wherein said oxygen scavenging composition comprises a solution of a reducing agent and a dissolved species of copper, said dissolved copper being present in an amount so as to provide, with respect to the total product within the package, from about 1 to 7 parts per million of copper as copper ion.

2. A packaged product in accordance with claim 1, wherein said reducing agent is ascorbic acid or salts or esters thereof, sodium sulfite, cysteine or catechol.

3. A packaged product in accordance with claim 1, wherein said oxygen scavenging composition further includes a chelating agent.

4. A packaged product in accordance with claim 3, wherein said chelating agent is selected from the group consisting of glycine, citric acid, EDTA, phosphate compounds and mixtures thereof.

5. A packaged product in accordance with claim 1, wherein said ingestible product is a food or a pharmaceutical.

6. A packaged product in accordance with claim 1, wherein said oxygen scavenging composition is dissolved in a vehicle selected from the group consisting of water, propylene glycol, glycerol, ethanol, fat and mixtures thereof.

7. A packaged product in accordance with claim 1, wherein said package is a jar or bottle with a lid or cap and the oxygen scavenging composition is incorporated in the lid or cap.

8. A packaged product in accordance with claim 1, wherein said oxygen scavenging composition in enrobed in an oxygen- and water-permeable material.

9. A packaged product in accordance with claim 1, wherein said copper is present in an amount of about 3 parts per million.

10. A packaged product in accordance with claim 6, wherein said vehicle is ethanol.

11. A packaged product in accordance with claim 1, wherein said oxygen scavenging composition comprises ascorbyl-6-palmitate and copper caprylate.

12. A packaged product in accordance with claim 2, wherein said reducing agent is ascorbic acid or a salt or ester thereof.

13. A packaged product in accordance with claim 6, wherein said vehicle is fat.

14. A packaged product in accordance with claim 6, wherein said vehicle is water.

15. A packaged product in accordance with claim 1, wherein said product is one containing fat, water or both fat and water and said reducing agent and said copper are dissolved in said fat and/or water of said product.

16. A packaged product in accordance with claim 1, wherein said product is a food.

17. A packaged product in accordance with claim 15, wherein said product is a food.

18. A packaged product in accordance with claim 1, wherein said copper is in the form of a $Cu^+$ or $Cu^{2+}$ ion.

* * * * *

UNITED STATES PATENT AND TRADEMARK OFFICE
CERTIFICATE OF CORRECTION

PATENT NO. : 5,270,337

DATED : December 14, 1993

INVENTOR(S) : Graf, Ernst

Page 1 of 2

It is certified that error appears in the above-identified patent and that said Letters Patent is hereby corrected as shown below:

| | |
|---|---|
| Column 4, Line 55 | Delete ".OH"<br>Insert -- ·OH-- |
| Column 4, Line 58 | Delete ".OH"<br>Insert --·OH-- |
| Column 4, Line 60 | Delete "." |
| Column 5, Line 4 | Delete ".OH"<br>Insert --·OH-- |
| Column 12, Line 43 | Delete "stabilizatioh"<br>Insert -- stabilization of -- |

UNITED STATES PATENT AND TRADEMARK OFFICE
CERTIFICATE OF CORRECTION

PATENT NO.  : 5,270,337

DATED       : December 14, 1993

INVENTOR(S) : Graf, Ernst

It is certified that error appears in the above-identified patent and that said Letters Patent is hereby corrected as shown below:

Column 12, Line 13            Delete "centrations"
                               Insert -- concentrations --

Signed and Sealed this

Twenty-fourth Day of May, 1994

*Attest:*

BRUCE LEHMAN

*Attesting Officer*    *Commissioner of Patents and Trademarks*